United States Patent [19]

Au et al.

[11] Patent Number: 5,872,111
[45] Date of Patent: Feb. 16, 1999

[54] COMPOSITIONS COMPRISING GLYCOSYLAMIDE SURFACTANTS

[75] Inventors: Van Au, New City, N.Y.; Bijan Harichian, South Orange, N.J.; Anthony Hung, New City, N.Y.; Robert Vermeer, Nutley, N.J.

[73] Assignee: Lever Brothers Company, Division of Conopco, Inc., New York, N.Y.

[21] Appl. No.: 858,750

[22] Filed: May 19, 1997

[51] Int. Cl.⁶ .................................................. A61K 31/70
[52] U.S. Cl. ............................ 514/62; 514/42; 536/18.7; 536/53; 536/55.2
[58] Field of Search ...................... 514/62, 42; 536/18.7, 536/53, 55.2

[56] References Cited

U.S. PATENT DOCUMENTS

| | | | |
|---|---|---|---|
| 4,574,122 | 3/1986 | Kruger et al. | 514/42 |
| 4,680,287 | 7/1987 | Lockholf et al. | 514/42 |
| 4,683,222 | 7/1987 | Stadler et al. | 514/42 |
| 4,686,208 | 8/1987 | Lockholf et al. | 514/42 |
| 4,699,899 | 10/1987 | Kruger et al. | 514/42 |
| 4,710,491 | 12/1987 | Lockholf et al. | 514/42 |
| 4,891,425 | 1/1990 | Lockholf et al. | 536/22 |
| 4,923,980 | 5/1990 | Blomberg | 536/55.3 |
| 5,070,190 | 12/1991 | Lockholf et al. | 536/22 |
| 5,362,480 | 11/1994 | Au et al. | 424/54 |
| 5,539,091 | 7/1996 | El Ghoul et al. | 536/22.1 |

FOREIGN PATENT DOCUMENTS

| | | |
|---|---|---|
| 155625 | 9/1985 | European Pat. Off. . |
| 515099 | 7/1993 | European Pat. Off. . |
| 2657611 | 8/1991 | France . |
| 2661413 | 10/1991 | France . |
| 2695127 | 3/1994 | France . |
| 43 29 094 A 1 | 2/1995 | Germany . |
| 62-209092 | 9/1987 | Japan . |

OTHER PUBLICATIONS

Kallin et al. Derivatizaton Procedure for Reducing Oligosaccharides, Part *3: Preparation Oligasaccharide Glycosylamines, and Their Conversion Oligosaccharide–AcrylamideCopoymers; J. Carbohydrate Chemistry 8(4), pp. 597–611 (1989).

Berndall, et al, Oxygen–Evolving Photosystem II Particles from Phormidium Laminosum; Methods in Enzymology, 167, pp. 272–280 (1988).

Onodera, et al., N–Acylation of Unsubstitued Glycosylamines; J. Org. Chem. (1960) 1322–25.

Costes, et al., Synthesis and Structural Analysis of Long Chain N–Acetyl–N–alkyllactosylamines a New Series of Surfactants Derived from Unprotected Lactose; Langmuir, 11, 3644–3647 (1995).

Lubineau, et al., Improved Synthesis of Glycosylaminesand a StraightforwardPreparation of N–acylglycosylamines as Carbohdrate–basedDetergents, Carbohydrate Research, 266, pp. 211–218 (1995).

Derwent Abstract of EP 155, 625; 9–25–85.
Derwent Abstract of JP–209092; 9–14–87.
Derwent abstract of DE 43–29 094 A1;3–2–95.

*Primary Examiner*—Douglas W. Robinson
*Assistant Examiner*—Evert White
*Attorney, Agent, or Firm*—Rimma Mitelman

[57] ABSTRACT

The present invention relates to novel detergent and/or personal wash compositions comprising glycosylamide surfactants.

3 Claims, 1 Drawing Sheet

COMPOSITIONS COMPRISING GLYCOSYLAMIDE SURFACTANTS

BACKGROUND OF THE INVENTION

The present invention relates to novel personal product or detergent compositions comprising glycosylamides as well as to novel processes for their preparation.

Carbohydrate based surfactants are potentially of great value because they represent a naturally-occurring source of renewable raw materials that are synthetically versatile, inexpensive, optically pure and environmentally friendly.

The glycosylamide compounds used in the novel detergent and personal wash compositions of the invention are themselves not novel. For example, U.S. Pat. No. 4,574,122 to Kruger et al. (assigned to Bayer), teaches substituted O-acyl glycosylamides for use in pharmaceutical compositions to stimulate the immune system's response and antibody production. Related U.S. Pat. No. 4,683,222 to Stadler et al. (assigned to Bayer) teaches N-glycosylated carbonamide derivatives which can be used for increasing immune system antibodies.

U.S. Pat. No. 4,680,287 to Lockhoff et al. (assigned to Bayer) also teaches these compounds, in this case used as growth promoters in live-stock feeding.

In U.S. Pat. No. 4,710,491, Lockhoff et al. (assigned to Bayer) teaches a method of combatting rheumatic diseases which comprises administering to a patient afflicted therewith with an amount of these compounds effective to combat the disease.

U.S. Pat. No. 4,891,425 to Lockhoff et al. (assigned to Bayer) teaches the use of these compounds as medicaments.

U.S. Pat. No. 4,923,980 to Blomberg teaches a process for the manufacture of a gel product, wherein a reducing sugar is covalently coupled to a matrix of a gel product. The matrix provides amino groups which can react with a reducing sugar to form a glycosylamine that is stabilized by acylation to form the corresponding glycosylamide. The invention has utility in affinity chromatography wherein the glycosylamide is coupled onto a solid carrier or matrix such as a gel.

J. Carbohydrate Chemistry 8 (4), 597–611, 1989 to Kallin et al. teaches the copolymerization of N-acryloylglycosylamines with acrylamide which are useful as antigens in immunoassays.

Methods in Enzymology 167, 272 (1988) to Bendall et al. teaches the use of N-methyl-N-decanoyl maltosylamine as a surfactant for photosystem II. While recognizing this compound to be surface-active, there is no teaching or suggestion that the compounds are used in detergent and/or personal product compositions.

J. Org. Chem. 25, 1322, (1960) to Onodera et al. teaches a method of acylating unsubstituted glycosylamines by reacting anhydrides with glycosylamines in methanol at 50° C.

French Patent No. 2,657,611 and Tetrahedron Letters 32 (12), 1557 (1991) to Ecole Superieure de Chimie de Rennes describes a process for preparing glycosylamides without prior protection of hydroxyl groups by using reagents (2-acylthio-5-methyl-1,3,4-thiadiazoles or 3-acyl-5-methyl-1,3,4-thiadiazole-2-(3H)-thiones) more selective than acyl chlorides. While recognizing these compounds are nonionic surface active agents, there is absolutely no teaching or suggestion that the compounds be used in detergent and/or personal product compositions.

French Patent No. 2,695,127 to Eridania Beghin-Say teaches a process for making glycosylamines in a diluted solvent and for preparing glycosylamides from glycosylamines and activated alkanoic acids. Again, there is absolutely no teaching or suggestion of using the glycosylamides as surfactants in detergent and/or personal product compositions.

French Patent No. 2,661,413 to Stepan teaches N-alkyl lactylamines and methods for preparing. Example 7 at pages 9–10 is an N-acetyl nonyl lactosylamine wherein the R' group is $COCH_3$ and therefore could be defined as an amide. There is no teaching or suggestion that such as amide could be used in detergent and personal product compositions. Indeed, in none of the examples which discuss surfactancy properties (i.e., surface active properties of Examples 1–5 and 8 of French Patent No. 2,661,413) is the amide exemplified in a detergent and/or personal product composition. Moreover, a general description of surface active properties (for the amines not the glycosylamides) is not a teaching or suggestion to use the compounds of the invention in detergent and/or personal product compositions in any event. Similarly, data about protein solubilization (Example 9) is neither a teaching or suggestion to use such compounds, particularly the glycosylamides of the invention, in detergent or personal product compositions.

Langmuir 11, 3644 (1995) to Costes et al. teach the preparation of N-acetyl-N-alkyl lactosylamines as surfactants for the extraction of proteins in pharmacological applications. Again, there is no teaching or suggestion to use glycosylamides in detergent and/or personal product compositions.

EP Application No. 0,515,283 (1992) to El Ghoul et al. (assigned to Stephan) teaches acetylated glycosylamides useful as solubilizing agents in the isolation of membranous proteins. Again, there is no teaching or suggestion to use glycosylamides in detergent and/or personal product compositions.

EP Application No. 0,550,099 (1993) to Au et al. (assigned to Unilever PLC) teaches the use of glycosylamides as antimicrobial agents (anti-plaque) in oral hygiene compositions. Again, there is no teaching or suggestion to use glycosylamides in detergent and/or personal product compositions.

Finally, in an article in Carbohydrate Research, 266, pp 211–218 (1995), Lubineau et al. teach preparation of N-acylglycosylamines as carbohydrate-based detergents. Some of the compounds made are set forth at top of page 214.

The compounds taught in this reference, (1) always have a hydrogen atom attached to the nitrogen ($R_2$ group) and (2) always have an $R_1$ group which is saturated and is not interrupted by a heteroatom (e.g., oxygen, sulfur or nitrogen).

Applicants have found that such compounds in which there is an attached hydrogen group at $R_2$, have much higher Krafft points, are far less soluble and consequently cannot be effectively formulated in detergent and personal product formulations.

By contrast, if the $R_2$ group is substituted with $C_1$ to $C_{30}$ alkyl group, preferably a $C_1$ to C8 alkyl group rather than hydrogen; or if the $R_1$ group contains a heteroatom such as O, S or N; or both; solubility is enhanced (lower Krafft point), such that the glycosamide compounds of the invention become more water soluble and can be readily and effectively formulated in detergent and personal product compositions.

Further, the fact that there is a hydrogen on the amide functional group and no heteroatom on the $R_1$ group (resulting in lower solubility) itself demonstrates that the compounds of Carbohydrate Research 266, pp 211–218 (1995), were not contemplated for use in detergent or personal product compositions. Also, novel methods of manufacture of glycosylamides have not been disclosed in the art.

In short, the use of the glycosylamide compounds of the subject invention in various detergent and personal product composition is simply unknown. The general surfactancy of the certain glycosylamide compounds are known, but this does not teach or suggest the use of the glycosylamide compounds of the invention in specific detergent and/or personal product compositions and, if anything, the use of such compounds in purely pharmaceutical applications actually teaches away from their use in the applications of the invention.

Thus, the ability to find a naturally derived, environmentally friendly, readily biodegradable, solid sugar based nonionic surfactant and a viable, cost-effective, commercially feasible method for their manufacture is a significant achievement.

Accordingly, it is an object of the present invention to provide new and improved detergent and personal product compositions that have excellent cleansing properties.

It is another object of the present invention to provide detergent and personal product compositions that have enhanced copious persistent foam.

It is another object of the invention to provide liquid detergent and personal product compositions that have enhanced thick viscosity which allows effective bottle packaging.

It is another object of the present invention to provide stable clear liquid detergent and personal product compositions which do not become turbid on produce sedimentation upon standing.

It is another object of the present invention to provide nonionic sugar based surfactants that dissolve readily and foam well in water.

It is still another object of the present invention to provide a viable, commercially feasible process for the manufacture of nonionic sugar based surfactants.

It is still another object of the present invention to provide an improved process for the manufacture of alkyl glycosylamides.

It is yet another object of the present invention to prepare alkyl glycosylamides in good yield, high purity and desirable color without hydroxyl group protection, oligomerization or polymerization.

These and other objects will become readily apparent from the detailed description that follows.

BRIEF SUMMARY OF THE INVENTION

In one embodiment, the present invention relates to personal product and/or detergent compositions comprising glycosylamides, a specific class of carbohydrate-based nonionic surfactant.

In a second embodiment, the present invention relates to a method of preparing glycosylamides in good color.

In a third embodiment, the present invention relates to a method of preparing glycosylamides in high yield and improved purity.

DETAILED DESCRIPTION OF THE INVENTION

Figure 1:
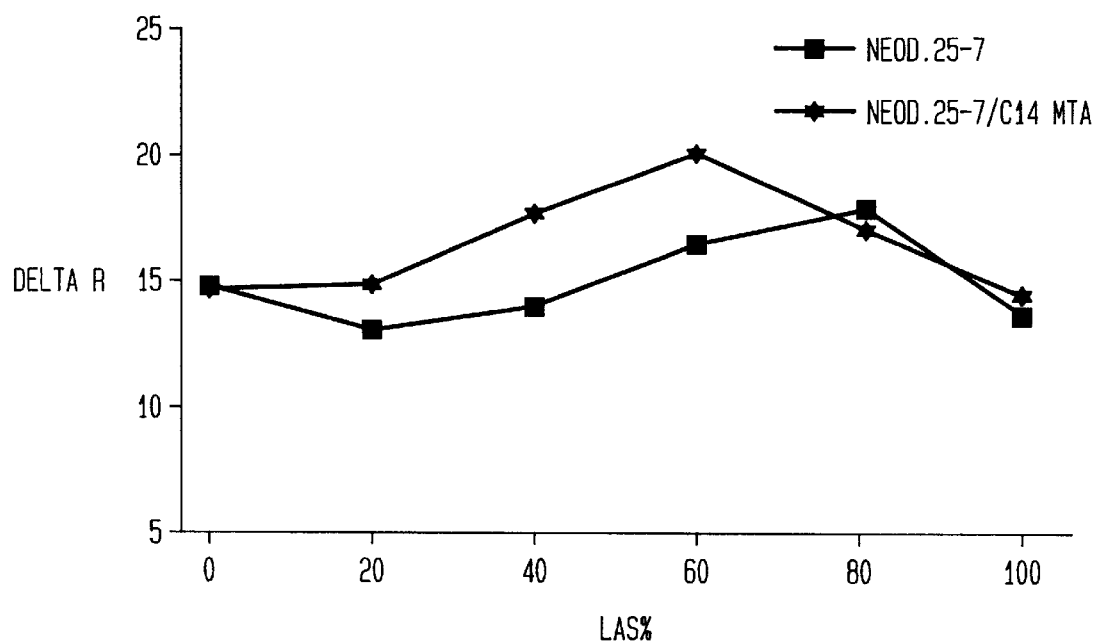
FIG. 1 shows detergency results in a ternary system comprising LAS (linear alkylbenzene sulfonate) and a mixture of 75% Neodol 25–7 ($C_{12}$–$C_{15}$ alkyl alcohol with 7 moles of ethylene oxide) and 25% $C_{14}$ MTA (N-acetyl tetradecyl maltosylamide). From FIG. 1 it can be seen that tertiary systems with maltosylamide performs about the same or slightly better than systems without maltosylamide.

The present invention relates to personal product and detergent compositions comprising environmentally friendly carbohydrate surfactants, in particular environmentally friendly nonionic surfactants such as alkyl glycosylamides.

Specifically, the glycosylamides of the invention have the following general structure:

$$\begin{array}{c} CH_2OH \\ \diagup \\ R_3-O \end{array} \begin{array}{c} \\ O \\ \\ HO \end{array} \begin{array}{c} R_2 \; O \\ | \; \; || \\ N-CR_1 \\ \\ OH \end{array}$$

wherein $R_1$ is hydrogen or an optionally substituted, straight-chain or branched, saturated or singly or multiply unsaturated alkyl radical having from 1 to 30 carbon atoms, it being possible for this radical ($R_1$) to also be interrupted by up to 25 or more, preferably from about 5 to about 15, more preferably from about 1 to about 2 O, S, and/or N heteroatoms as well as mixtures thereof.

When the chain is interrupted by N, this nitrogen may carry either a H or a $C_1$–$C_{30}$, preferably $C_1$–$C_8$ alkyl radical or a carbonyl alkyl radical (COR), the latter COR group can have 1–30, preferably 1–8 carbon atoms and can also be interrupted by O, S and/or N heteroatoms, as well as mixtures thereof.

Preferred compounds of the formula I are those in which $R_1$ represents an alkyl or alkenyl radical having 1 to 30 carbon atoms, more preferably 6 to 21 carbon atoms. Examples of saturated radicals which may be mentioned in this context are methyl, butyl, t-butyl, n-octyl, n-tetradecyl, n-nonadecyl, docosyl, ethylpentyl, methyldecyl, isopropyldecyl or methyltridecosyl and the like.

Examples of unsaturated radicals in the compounds used according to the invention are vinyl, 1-propenyl, 2-propenyl, 1-butenyl, 2-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-decenyl, 5-decenyl, 9-decenyl, 8-heptadecenyl, 1,3-butadienyl, 1,3-pentadienyl, 1,4-pentadienyl, 2,4-pentadienyl, 8,11-heptadecadienyl, 8,11,14-heptadecatrienyl and the like.

The unsaturated hydrocarbon radicals can be in the form of pure cis or trans isomers or as a mixture of isomers.

Examples of compounds which are used according to the invention and in which the hydrocarbon radicals $R_1$ in formula I are interrupted by O, S and N heteroatoms or groups of corresponding atoms, or are substituted by groups containing these atoms or by halogen atoms are the methoxyethyl, methyloxypropyl, hydroxyheptadecyl, hydroxybutyl, ethylaminodecyl, N-methylaminodecyl, fluoromethyl, β-hydroxytridecyl, mercaptoethyl, methylamidododecyl, cocoaminopropyl, cocooxypropyl, cocoacylamidopropyl, cocopoly(oxyethyl)oxypropyl, $C_8$–$C_{18}$ oxypropylaminopropyl or $C_8$–$C_{18}$ oxypropylamidoethylpropyl, cocopoly(oxypropyl) oxyethyl radicals and the like.

Examples of O, S and N heteroatoms include, but are not limited to —O— (ether); —OH (hydroxy); —S— (sulfur); —SO— (sulfurmonoxide); —SO$_2$— (sulfurdioxide); —NH—, —NR$_1$— (amino); —NHCO—, —CONH—, NRCO—, or —CONR$_1$— (amido); —$^+$NH$_2$—, —$^+$NHR$_1$ or —$^+$N(R$_1$)$_2$— (quaternary); COO or OOC (ester) and the like as well as mixtures thereof.

The hydrocarbon radicals $R_1$ in formula I can also contain phenyl radicals, it also being possible for these phenyl radicals to be optionally substituted by one to three substituents from the series comprising nitro and lower alkyl or by 1 to 5 halogen atoms. Preferably, $R_1$ is a straight chain $C_1$ to $C_{30}$ alkyl or alkenyl group, more preferably a $C_6$ to $C_2$, alkyl group.

$R_2$ can be hydrogen when $R_1$ is interrupted by O, S or N heteroatom but preferably is a straight chain or branched, saturated or singly or multiply unsaturated alkyl, cycloalkyl, alkylcycloalkyl or arylalkyl radical having up to 30 carbon atoms, it also being possible for individual methylene or methane groups in the radical $R_2$ to be replaced by up to 25 or more O, S,N, NH or N-lower alkyl heteroatom groups. Furthermore it is possible for individual hydrogen atoms in the alkyl, cycloalkyl or arylalkyl radicals to be substituted by up to 25 oxygen containing groups or halogen atoms.

If $R_2$ is hydrogen, $R_1$ must have an interrupting heteroatom group. If there is no interrupting heteroatom group or $R_1$ and $R_2$ is hydrogen, the compound would not be sufficiently soluble for the purpose of the invention. Of course, it should be understood that compounds of the invention may both have a $C_1$ to $C_{30}$ $R_2$ groups attached to nitrogen and have and interrupting heteroatom in the $R_1$ group, but not a hydrogen on the $R_2$ group and a saturated $R_1$ alkyl group.

Examples in which $R_2$ in formula I represents a straight chain or branched, optionally singly or multiply unsaturated alkyl radicals are those mentioned for $R_1$.

The following may be particularly mentioned: methyl, ethyl, propyl, hexyl, decyl, dodecyl, tetradecyl, hexadecyl, octadecyl, dodosyl, myrisyl, ethylhexyl, isobutyl, propenyl, octenyl, hexadienyl, docosenyl, dimethylhexenyl and 2-(cyclohexyl)ethyl. The unsaturated hydrocarbons can be in the form of pure cis or trans isomers or as a mixture of isomers. Examples of hydrocarbon radicals $R_2$ substituted or interrupted by groups containing oxygen atoms are hydroxypropyl, hydroxydimethyloctyl, methoxybutyl, methoxypropyl and butoxypropyl. Examples of hydrocarbon radicals interrupted by N is cocoaminopropyl, tallowaminopropyl, dimethylaminopropyl, dimethylaminoethyl and dodecylamidopropyl. An example of a hydrocarbon radical substituted by halogen which may be mentioned is trifluoromethylethyl.

Examples of arylalkyl for $R_2$ in formula I are aryl lower alkyl, such as benzyl, phenylethyl or phenylhexyl, it being possible for the phenyl nucleus optionally to be substituted singly or multiply, preferably singly or doubly, for example by lower alkyl, trifluoromethyl, halogen, hydroxyl or lower alkoxy.

Lower alkyl or alkoxy groups are to be understood to be those radicals which contain 1 to 5, preferably 1 to 3, carbon atoms.

Preferably $R_2$ is straight chain $C_1$ to $C_{24}$ alkyl, more preferably a $C_1$ to $C_8$ group.

$R_3$ is a glycosyl radical (i.e., reducing glycol sugar bonded to the oxygen atom). Glycosyl radicals according to the invention are understood to be monosaccharide, disaccharide and oligosaccharide radicals, in particular monosaccharides and disaccharides in which one or more hydroxyl groups can optionally be replaced by amino groups, acylamido groups, azido groups, hydrogen, nitro, thiol groups or lower alkoxy or halogen, and it also being possible for the glycosyl radicals to be in the form of the corresponding uloses, ulose derivatives, uronic acids or of uronic acid derivatives.

According to the invention, the glycosyl radicals $R_3$ in formula I are preferably in the pyranosyl or furanosyl form, the relevant monosaccharide, disaccharide or oligosaccharide radicals preferably being constructed of pentoses, hexoses and heptoses.

Examples of monosaccharide radicals in the compounds used according to the invention are glucopyranosyl, galactopyranosyl, mannopyranosyl, glucofuranosyl, ribofuranosyl, arabinopyranosyl, or lyxopyranosyl or D-glycero-D-glucoheptopyranosyl radicals. Examples of disaccharide and oligosaccharide radicals which may be mentioned are maltosyl, maltotriosyl, maltotetraosyl, lactosyl, cellobiosyl, melibiosyl or 6-O-(α- or β-ribofuranosyl) glucopyranosyl radicals, that is to say carbohydrate systems which are constructed of sugars having different C numbers, and in which the sugars can be in the pyranose and/or furanose form. The glycosidic bonds between the individual sugar units can be in the α- and/or β-form, and the glycosidic linkage of the individual sugar units can, starting from an anomeric carbon atom, take place both via the primary OH group and via one of the secondary hydroxyl groups of the saccharide moiety which is functioning as an aglycone.

Examples of monosaccharide, disaccharide and oligosaccharide radicals in which one or more OH groups are replaced by amino groups, acylamido groups, azido groups, hydrogen, nitro, thiol groups, lower alkoxy or halogen which may be mentioned for the compounds used according to the invention are 2-acetylamido-2-deoxyglucopyranosyl-, 2-amino-2-deoxyglucopyranosyl-, 4-azido-4-deoxyglucopyranosyl-, 4-stearoylamido-4-deoxy-D-glycopyranosoyl-, 4-dodecoylamido-4-deoxy-D-glucopyranosyl-, 6-hexadecanoylamido-6-deoxy-D-galactopyranosyl-, 2,6-diamino-2,6-dideoxyglucopyranosyl-, 6,6-diamino-6,6'-dideoxymaltosyl-6-amino-6,6'-dideoxylactosyl, 6-deoxymannopyranosyl-, 2-deoxyribofuranosyl-, fucosyl, 5-fluoro-5-deoxyribofuranosyl-, 6-O-methylglucopyranosyl, 6-deoxy-6-thioglucopyranosyl and 3-deoxy-3-nitrogalactopyranosyl.

When the glycosyl radicals are in the form of uronic acids or uronic acid derivatives, then they are glycuronic acids having a free carboxyl group or having a carboxyl group esterified by alkyl, or they are glycuronamide derivatives having an unsubstituted or substituted nitrogen atom. Examples of appropriate sugars are galacturonic acid, methyl glucuronate or N-dodecylglucuronamide.

Preferably, $R_3$ is a monosaccharide selected from the group consisting of glycopyranosyl, galactopyranosyl and mixtures thereof.

Specific examples of a monosaccharide alkyl glycosylamide compounds of the invention include coconut N-methyloxypropyl D-glucosylamide; coconut N-methyl D-glucosylamide; coconut -N,N'dimethylamino-N'-ethyl D-glucosylamide; tallow N-methyl D-glucosylamide; dodecyl N-propyl D-glucosylamide; dodecyl N-hydroxyethyl D-glucosylamide; tetradecyl N-methyloxypropyl D-glucosylamide; acetyl N-tetradecyl D-glucosylamide; propyl N-dodecyl D-glucosylamide; acetyl N-$C_8/C_{10}$ oxypropyl D-glucosylamide; acetyl N-$C_{12}$–$C_{15}$ tetra(oxyethylene)oxypropyl D-glucosylamide; coconut N-methyl D-glucosylamide trioxyethylene ether; ethyl N-$C_{12}$–$C_{15}$ oxypropylamidopropyl-N'-ethyl D-glucosylamide; coconut -N,N-dimethylpropyl D-glucosylamide; sodium dodecyl N-methyl D-glucosylamide monosulfate; and potassium tetradecyl N-methyl D-glucosylamide monophosphate.

Specific examples of a disaccharide alkyl glycosylamide compound of the invention include coconut N-methyl D-maltosylamide; oleyl N-methyl D-maltosylamide; ethyl N-tetradecyl D-maltosylamide; propyl N-dodecyloxypropyl D-maltosylamide; and coconut N-hydroxyethyl D-lactosylamide.

Other examples of compounds of the invention are set forth below:

dialkyl D-erythrosylamide
dialkyl D-threosylamide
dialkyl D-ribosylamide
dialkyl D-arabinosylamide
dialkyl D-xylosylamide
dialkyl D-lyxosylamide
dialkyl D-allosylamide
dialkyl D-altrosylamide
dialkyl D-idosylamide
dialkyl D-talosylamide
dialkyl D-glucosylamide
dialkyl L-glucosylamide
dialkyl D-galactosylamide
dialkyl L-galactosylamide
dialkyl D-mannosylamide
dialkyl D-gulosylamide
dialkyl D-fructosylamide
dialkyl L-fructosylamide
dialkyl D-sorbosylamide
dialkyl L-sorbosylamide
dialkyl D-isomaltosylamide
dialkyl D-isomaltulosylamide
dialkyl D-trehalulosylamide
dialkyl D-ribulosylamide
dialkyl D-xylulosylamide
dialkyl D-3-ketosucrosylamide
dialkyl D-leucrosylamide
dialkyl D-lactulosylamide
dialkyl D-psicosylamide
dialkyl D-rhamnosylamide
dialkyl D-maltosylamide
dialkyl L-maltosylamide
dialkyl D-lactosylamide
dialkyl L-lactosylamide
dialkyl D-melibiosylamide
dialkyl D-cellobiosylamide
dialkyl D-cellulosylamide
dialkyl D-dextrosylamide
dialkyl D-glucosylamide monooxyethylene ether
dialkyl D-glucosylamide dioxyethylene ether
dialkyl D-glucosylamide trioxyethylene ether
dialkyl D-glucosylamide pentaoxyethylene ether
dialkyl D-glucosylamide hexaoxyethylene ether
dialkyl D-glucosylamide octaoxyethylene ether
dialkyl D-glucosylamide nonaoxyethylene ether
dialkyl D-glucosylamide decaoxyethylene ether
dialkyl D-glucosylamide trioxypropylene ether
dialkyl D-glucosylamide trioxypropylene dioxyethylene ether
dialkyl D-glucosylamide dioxyethylene trioxypropylene ether
dialkyloxy(monooxyethylene) D-glucosylamide
dialkyloxy(dioxyethylene) D-glucosylamide
dialkyloxy(trioxyethylene) D-glucosylamide
dialkyloxy(pentaoxyethylene) D-glucosylamide
dialkyloxy(heptaoxyethylene) D-glucosylamide
dialkyloxy(decaoxyethylene) D-glucosylamide
dialkyloxy(pentaoxypropylene) D-glucosylamide
dialkyloxyethylamino D-glucosylamide
dialkyloxyethylamido D-glucosylamide
dialkyloxyethylsulfo D-glucosylamide; and
dialkyloxyethylsulfodioxy D-glycosylamide;
wherein the alkyl group is from 1 to 30 carbon atoms.

The glucosylamide surfactants of the present invention can also be sulfated with chlorosulfonic acid, sulfur trioxide, sulfur trioxide/Lewis base complexes, oleum, sulfuric acid, sulfamic acid and the like as well as mixtures thereof, to give a series of novel sulfated sugar based anionic surfactants.

The glucosylamide surfactants of the present invention can also be phosphorylated with phosphorus oxychloride, phosphorous pentoxide, polyphosphoric acid, phosphoric acid, phosphorus trichloride and the like as well as mixtures thereof, to give a series of novel phosphated sugar based esters (mono-, di-, and triesters as well as mixtures thereof) as anionic surfactants.

The glycosylamide surfactants of the present invention can also be ethoxylated, propoxylated and mixtures thereof.

The glycosylamides used in the composition of the invention have been found to have effective surface-active properties (i.e., critical micelle concentrations; Krafft Point; foaming; detergency) indicating that they are equal to or better than other well known nonionic surfactants which are based on petrochemicals (e.g., alkoxylated surfactants from the Neodol TM series from Shell). They are viable, environmentally friendly alternative for more traditional nonionic surfactants.

While not wishing to be bound by theory, the higher solubility of the substituted glycosylamides of the invention relative to unsubstituted glycosylamides is believed to be due, in great part, to the $R_2$ preferably not being hydrogen, (unless $R_1$ is interrupted with a heteroatom) but rather a straight chain alkyl group, for example, $C_1$ to $C_8$ alkyl group, which can disturb the packing behavior of these materials in the crystalline state making such compounds more readily soluble in water as well as in detergent and personal product compositions.

In addition, the surfactants of the invention may be used as cosurfactants with other nonionic surfactants or with other surfactants (e.g., cationic, anionic, zwitterionic, amphoteric) that are known or become known and are used in personal product and/or detergent formulations.

COMPOSITIONS

The personal product compositions of the invention may be, for example, toilet bar compositions, facial or body cleansing compositions, shampoos for hair or body, conditioners (hair and body conditioners), cosmetic compositions, shaving creams, shaving lotion compositions, shower gel compositions and the like.

The detergent compositions of the invention may be, for example, heavy duty detergent powders and liquids, light duty liquids and the like.

In one embodiment of the invention, the glycosylamide surfactant of the invention may be used, for example, in a toilet bar i.e., soap and/or detergent bar) formulation.

Typical toilet bar compositions are those comprising fatty acid soaps used in combination with a detergent other than fatty acid soap and free fatty acids. It should be noted that the composition may comprise fatty acid soap and may be based merely on actives other than fatty acid soap. Mildness improving salts, such as alkali metal salt or isethionate are also typically added. In addition other ingredients, such as germicides, perfumes, colorants, pigments, suds boosting salts and anti-mushing agents may also be added.

Fatty acid soaps are typically alkali metal or alkanol ammonium salts of aliphatic alkane or alkene monocarboxylic acids. Sodium, potassium, mono-, di- and tri-ethanol ammonium cations, or combinations thereof, are suitable for purposes of the invention. The soaps are well known alkali metal salts of natural or synthetic aliphatic (alkanoic or alkenoic) acids having about 8 to 22 carbons, preferably 12 to about 18 carbons. They may be described as alkali metal carboxylates of acrylic hydrocarbons having about 12 to 22 carbons.

Examples of soap which may be used may be found in U.S. Pat. No. 4,695,395 to Caswell et al, and U.S. Pat. No. 4,260,507 (Barrett), both of which are incorporated herein by reference.

In a soap-based bar, fatty acid soaps will generally comprise greater than 25% of the composition, generally from 30–95%. Preferably, the amount of soap will range from 40 to 70% by weight of the composition. In a bar based on other actives, soap may comprise 0–50% by weight. In general $C_8$ to $C_{24}$ fatty acid comprises 5–60% of the composition. The compositions will also generally comprise a non-soap detergent which is generally chosen from anionic, nonionic, cationic, zwitterionic or amphoteric synthetic detergent material or mixtures thereof. These surfactants are all well known in the art and are described, for example, in U.S. Pat. Nos. 4,695,395 and 4,260,507 discussed above. One preferred non-soap anionic is a $C_8$ to $C_{22}$ alkyl isethionate. These ester may be prepared by the reaction between alkali metal isethionate and mixed aliphatic fatty acids having from 8 to 22 carbons. The non-soap actives may comprise from 0 to 50% of the composition.

A certain amount of free fatty acids of 8 to 22 carbons are also desirably incorporated into soap compositions to act as superfatting agents or as skin feel and creaminess enhancers. If present, the free fatty acids comprise between 1 and 40% of the compositions.

A preferred salt which may be added to soap compositions is a simple unsubstituted sodium isethionate. This may be present as 0.1 to 50% of the composition, preferably 0.5% to 25%, more preferably 2% to about 15% by weight. Other mildness co-actives which may be used include betaine compounds or ether sulphates. These also may be present at 0.1 to 50% of the composition, preferably 0.5% to 25%.

The sulfate ester surfactant may comprise of up to 45% by weight of the composition (as the monoester), preferably 25% to 40%, and 0.01% to 10% of the composition (as the diester), preferably 0.01% to 5%.

Glycosylamides may comprise 0.1 to 45% by wt. of the bar composition, preferably 0.5 to 20% by wt.

Other optional ingredients which may be present in toilet bar compositions are moisturizers such as glycerin, propylene glycol, sorbitol, polyethylene glycol, ethoxylated or methoxylate ether of methyl glucose etc; water-soluble polymers such as collagens, modified cellulases (such as Polymer JR$^{(R)}$), guar gums and polyacrylates; sequestering agents such as citrate, and emollients such as silicones or mineral oil. Another useful set of ingredients are various cosurfactants and non-soap detergents.

In a second embodiment of the invention, the glycosylamide surfactant of the invention may be present in a facial or body cleansing composition. Examples of such cleaning compositions are described, for example, in U.S. Pat. No. 4,812,253 to Small et al, and U.S. Pat. No. 4,526,710 to Fujiwara, both of which are hereby incorporated by reference.

Typically, cleansing compositions will comprise a fatty acid soap together with a non-soap surfactant, preferably a mild synthetic surfactant. Cleaning compositions will also generally include a moisturizer or emollient and polymeric skin feel and mildness aids. The compositions may further optional include thickener (e.g., magnesium aluminum silicate, carbopol), conditioners, water soluble polymers (e,g., carboxymethyl cellulose), dyes, hydrotropes, brighteners, perfumes and germicides.

The fatty acid soaps used are such as those described above in uses in detergent bar formulations. These soaps are typically alkali metal or alkanol ammonium salts of aliphatic or alkene monocarboxylic salts. Sodium, potassium, mono-, di- and triethanol ammonium cations, or combinations thereof are suitable Preferred soaps are 8 to 24 carbon half acid salts of, for example triethanolamine.

Surfactants can be chosen from anionic, nonionic, cationic, zwitterionic or amphoteric materials or mixtures thereof such as are described in U.S. Pat. No. 4,695,395 mentioned above, or in U.S. Pat. No. 4,854,333 to Inman et al., hereby incorporated by reference.

Moisturizers are included to provide skin conditioning benefits and improve mildness. This term is often used as synonymous with emollient and is then used to describe a material which imparts a smooth and soft feeling to skin surface.

There are two ways of reducing water loss from the stratum corneum. One is to deposit on the surface of the skin an occlusive layer which reduces the rate of evaporation. The second method is to add nonocclusive hygroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers are suitable the present invention. Some examples of moisturizers are long chain fatty acids, liquid water-soluble polyols, glycerin, propylene glycol, sorbitol, polyethylene glycol, ethoxylated/propoxylated ethers of methyl glucose (eg., methyl gluceth-20) and ethoxylated/propoxylated ethers of lanolin alcohol e.g., Solulan-75).

Preferred moisturizers are coco and tallow fatty acids. Some other preferred moisturizers are the nonoclusive liquid water soluble polyols and the essential amino acid compounds found natural in the skin.

Other preferred nonocclusive moisturizers are compounds found to be naturally occurring in the stratum corneum of the skin, such as sodium pyrrolidone carbolylic acid, lactic acid, urea, L-proline, guanidine and pyrrolidone. Examples of other nonocclusive moisturizers include hexadecyl, myristyl, isodecyl isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—a Critical Evaluation," by J. Mausner Cosmetics & Toiletries, May 1981, incorporated herein by reference.

The polymeric skin feel and mildness aids useful in the present invention are the cationic, anionic, amphoteric, and the nonionic polymers used in the cosmetic field. Reduced skin irritation benefits as measured by patch testing of cationic and nonionic types of polymers are set out in "Polymer JR for Skin Care" Bulletin, by Union Carbide, 1977. The cationics are preferred over the others because they provide better skin feel benefits.

The amount of polymeric skin feel and mildness aids found useful in the composition of the present invention is from about 0.01 % to about 5%, preferably from about 0.3% to about 4%. In bar compositions with less than 5.5% soap, the polymer is used at a level of 2% to 5%, preferably 3% or more.

Other types of high molecular weight polymeric skin feel and skin mildness aids, such as nonionic guar gums, Merquats 100 and 550, made by Merck & Co, Inc.; Jaguar C-14-S made by Stein Hall; Mirapol A15 made by Miranol Chemical Company, Inc,; and Galactasol 811, made by Henkel, Inc,; plus others, are usable. The aid also provides enhanced creamy lather benefits.

The nonionic polymers found to be Useful include the nonionic polysaccharides, e,g, nonionic hydroxypropyl guar gums, offered by Celanese Corp. A preferred nonionic hydroxypropyl guar gum material is Jaguar HP-60 having molar substitution of about 0.6, another class of useful nonionics is the cellulosic nonionic polymers, e.g., HEC and CMC.

The cationic polymers employed in this invention also provide a desirable silky, soft, smooth in-use feeling. The preferred level for this invention is 0.1–5% of the composition. There is reason to believe that the positively charged cationic polymers can bind with negatively charges sites on the skin to provide a soft skin feel after use. Not to be bound by any theory, it is believed that the greater the charge density of the cationic polymer, the more effective it is for skin feel benefits, Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., Sta-Lok$^R$ 300 and 400 made by Staley, Inc.

A more complete list of cationic polymers useful in the present invention is described in U.S. Pat. No. 4,438,095, to Grollier/Allec, issued Mar. 20, 1984, incorporated herein by reference. Some of the more preferred cationics are listed in Column 3, Section 2; Column 5, Section 8; Column 8, Section 10; and Column 9, lines 10–15 of the Grollier/Allec patent, incorporated herein by reference.

The glycosylamide may be used in the cleanser in an amount comprising 0.1 to 25%, preferably 0.5 to 15% by wt. of the composition.

In a third embodiment of the invention, the glycosylamide surfactant of the invention may be used, for example, in a bar or body shampoo. Examples of such compositions are described in U.S. Pat. No. 4,854,333, to Inman and U.S. Pat. No. 4,526,710 to Fujiwara, both of which are hereby incorporated by reference.

The shampoo compositions which may be used typically comprise a surfactant selected from any one of a wide variety o surfactants known in the art (such as those described in U.S. Pat. No. 4,854,333, incorporated herein by reference). The shampoo compositions m ay additionally comprise a compound considered useful for treating dandruff, e.g., selenium sulfide.

The compositions all may also optionally comprise a suspending agent, for example, any of several acyl derivative materials or mixtures thereof. Among these are ethylene glycol esters of fatty acids having 16 to 22 carbons, Preferred suspending agents include ethylene glycol stearates, both mono and distearate. Preferred alkanol amides are stearic monoethanolamide, stearic diethanolamide and stearic monoisopropanolamide. Still other long chain acyl derivatives include long chain esters of long chain fatty acids (e.g., stearyl stearate, cetyl palmitate), glyceryl esters (e,g. glyceryl distearate), and long chain esters of long chain alkanol amides (e.g., stearamide DEA distearate, stearamide MEA stearate).

Still other suitable suspending agents are alkyl (16 to 22 carbon) dimethyl amine oxides, such as stearyldimethyl amine oxide. If the compositions contain an amine oxide or a long chain acyl derivative as a surfactant, these components may also provide the suspending function and additional suspending agent may not be needed.

Xanthan gum is another agent used to suspend, for example, selenium sulfide which may be in the present compositions. This biosynthetic gum material is commercially available and is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4,7% acetyl. Supplemental information on these agents is found in Whistler, Roy L. (Editor), *Industrial Gums—Polysaccharides and Their Derivatives* New York: Academic Press, 1973. Kelco, a Division of Merck & Co., Inc, offers xanthan gum as Keltrol$^{(R)}$.

A particularly preferred suspending system comprises a mixture of xanthan gum, present at a level of from about 0.05% to about 1.0%, preferably from about 0.2% to about 0,4%, of the compositions, together with magnesium aluminum silicate ($Al_2Mg_8Si_2$) present at a level of from about 0.1% to about 3.0%, preferably from about 0.5% to about 2.0%, of the compositions.

Magnesium aluminum silicate occurs natural in such smectite minerals as colerainite, saponite and sapphire. Refined magnesium aluminum silicates useful herein are readily available, for example as veegum, manufactured by R. T. Vanderbilt Company, Inc. Mixtures of suspending agents are also suitable for use in the compositions of this invention.

Other useful thickening agents are the cross-linked polyacrylates such as those manufactured by B.F. Goodrich and sold under the Carbopol(R) tradename, Another optional component for use in the present compositions is an amide. The amide used in the present compositions can be any of the alkanolamides of fatty acids know for use in shampoos. These are generally mono- and diethanolamides of fatty acids having from about 8 to 24 carbon atoms. Preferred are coconut monoethanolamide, lauric diethanolamide and mixtures thereof. The amide is present at a level of from about 1% to about 10% of the compositions.

The compositions may also contain nonionic polymer material which is used at a low level to aid in dispersing particles. The material can be any of a large variety of types including cellulosic materials such as hydroxypropylmethyl cellulose, carboxymethyl cellulose, hydroxyethyl cellulose and sodium carboxymethyl cellulose as well as mixtures of these materials. Other materials include alginates, polyacrylic acids polyethylene glycol and starches, among many others. The nonionic polymers are discussed in detail in *Industrial* Gums, edited by Roy L. Whistler, Academic Press, Inc., 1973, and *Handbook of Water-Soluble Gums and Resins*, edited by Robert L. Davidson, McGraw-Hill, Inc., 1980. Both of these books in their entirety are incorporated herein by reference.

When included, the nonionic polymer is used at a level of from about 0.001% to about 0.1%, preferably from about 0.002% to about 0.05%, of the composition. Hydroxypropyl methyl cellulose is the preferred polymer.

Another suitable optional component useful in the present compositions is a nonvolatile silicone fluid.

The nonvolatile silicone fluid may be either a polyalkyl siloxane, a polyaryl siloxane, a polyalkylaryl siloxane or a polyether siloxane copolymer and is present at a level of from about 0.1% to about 10.0%, preferably from about 0.5% to about 5.0%, Mixtures of these fluids may also be used and are preferred in certain executions. The dispersed silicone particles should also be insoluble in the shampoo matrix. This is the meaning of "insoluble" as used herein.

The essential nonvolatile polyalkyl siloxane fluids that may be used include, for example, polydimethyl siloxanes with viscosities ranging from about 5 to about 600,000 centistokes at 25° C. These siloxanes are available, for example, from the General Electric Company as the Viscasil series and from Dow Corning as the Dow Corning 200 series. The siloxane viscosity can be measured by means of a glass capillary viscometer as set forth in Dow Corning Corporate Test Method CTM0004, Jul. 20, 1970. Preferably the viscosity of the these siloxanes range from about 350 centistokes to about 100,000 centistokes.

The essentially nonvolatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

Suitable silicone fluids are described in U.S. Pat. No. 2,826,551, Geen; U.S. Pat. No. 3,946,500, Jun. 22, 1976, Drakoff U.S. Pat. No. 4,364,837, Pader; and British Pat. No. 849,433, Woolston. All of these patents are incorporated herein by reference. Also incorporated herein by reference is Silicon Compounds, distributed by Petrarch Systems, Inc., 1984. This reference provides a very good listing of suitable silicone.

Another silicone material useful is silicone gum. Silicone gums are described by Petrarch and others including U.S. Pat. No. 4,152,416, May 1, 1979, Spitzer, et al., and Noll, *Chemistry and Technology of Silicones*, New York, academic Press, 1968. Useful silicone gums are also described in General Electric Silicone Rubber Product Data Sheets SE 30, SE 33, SE 54 and SE 76. All of these references are incorporated herein by reference. "Silicone gum" materials denote high molecular weight polydiorganosiloxanes having a mass molecular weight of from about 200,000 to about 1,000,000, Specific examples include polydimethylsiloxane, (polydimethylsiloxane) (methylvinylsiloxane) copolymer, poly(dimethylsiloxane) (diphenyl) (methylvinylsiloxane) copolymer, and mixtures thereof. Mixtures of silicone fluids and silicone gums are also useful herein.

The shampoos herein can contain a variety of other nonessential optional components suitable for rendering such compositions more formulatable, or aesthetically and/or cosmetically acceptable. Such conventional optional ingredient are well-known to those skilled in the art and include, e.g. preservatives, such as benzyl alcohol, methyl paraben, propyl paraben, and imidazolinidyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers, such as block polymers of ethylene oxide and propylene oxide such as Pluronic F88 offered by BaSa Wyandotte, sodium chloride, sodium sulfate, propylene glycol, and ethyl alcohol; pH adjusting agents, such as citric acid, succinic acid, phosphoric acid, sodium hydroxide, sodium carbonate; perfumes; dyes; and sequestering agents, such as disodium ethylenediamine tetraacetate. Such agents generally are used individually at a level of from about 0.01% to about 10%, preferably from about 0.5 to about 5.0%, of the composition.

A typical shampoo composition might comprise (percentage by weight:

(1) Glycosylamide 0.01–35%;
(2) Anionic coactive 0–10%;
(3) Amphoteric coactive 0–10%
(4) Lauramide MEA 0–5%;
(5) Thickener 0–5%;
(6) Fragrance 0–2%;
(7) Preservative 0–1%; and Remainder water In a fourth embodiment of the invention, the glycosylamide surfactant of the invention may be used in a conditioner composition such as is taught and described in U.S. Pat. No. 4,913,828 to Caswell et al., which is hereby incorporated by reference.

More particularly, conditioner compositions are those containing a conditioning agent (e.g. alkylamine compounds) such as those described in U.S. Pat. No. 4,913,828.

In a fifth embodiment of the invention, the surfactant may be used in a cosmetic composition, such as is taught and is described in EP 0 371 803.

Such compositions generally comprise thickening agents preservatives and further additions.

The composition may comprise polymer thickener in an amount sufficient to adjust the viscosity of the composition, so as to facilitate dispensing it conveniently onto the body surface.

Examples of polymer thickeners include: anionic cellulose materials, such as sodium carboxy methyl cellulose; anionic polymers such as carboxy vinyl polymers, for example, Carbomer 940 and 941; nonionic cellulose materials, such as methyl cellulose and hydroxypropylmethyl cellulose; cationic cellulose materials, such as Polymer JR 400; cationic gum materials, such as Jaguar C13 S; other gum materials such as gum acacia, gum tragacanth, locust bean gum, guar gum and carrageenan; proteins, such as albumin and protein hydrolysates; and clay materials, such as bentonite, hectorite, magnesium aluminum silicate, or sodium magnesium silicate.

Generally, the thickening agent may comprise from 0.05 to 5%, preferably 0.1 to 1% by weight of the composition.

The composition according to the invention can also optionally comprise a preservative to prevent microbial spoilage.

Examples of preservatives include:

(i) Chemical preservatives, such as ethanol, benzoic acid, sodium benzoate, sorbic acid, potassium sorbate, sodium propionate and the methyl, ethyl, propyl and butyl esters of p-hydroxybenzoic acid 2-bromo-2-nitropropane-1,3-diol, phenoxyethanol, dibromodicyanobutane, formalin and Tricolsan. The amount of chemical preservative optionally to be incorporated in the composition according to the invention will generally be from 0.05 to 5%, preferably from 0.01 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, sufficient amount should be incorporated in the composition according to the invention to reduce the water activity from 1 to <0.9, preferably to <0.85 and most preferably <0.8, the lowest of these values being that at which yeasts, molds and fungi will not proliferate.

The composition can also contain other optional adjuncts which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually with at least one other cosmetically-acceptable vehicle, Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1,2-diol, butane-1,3-diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oil such as dimethylpolysiloxane, di-n-butyl sebacate, isopropyl myristate, isopropyl palnitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristates.

Propellants, such as trichlorofluoromethane, dichlorodifluoromethane, dichlorotetrafluoromethane, monochlorodifluoromethane, trichlorotrifluoromethane, propane, butane, isobutane, dimethyl ether, carbon dioxide, nitrous oxide Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulfoxide, dimethyl formamide, tetrahydrofuran and the like.

Humectants, such as glycerin, sorbitol, sodium 2-pyrrolidone-5-carboxylate, soluble collagen, dibutyl phthalate gelatin.

Powders, such as chalk, talc, fullers earth, kaolin, starch, gums, colloidal silicon dioxide, sodium polyacrylate, tetra alkyl and/or trialkylarylammonium smectites, chemical modified magnesium aluminum silicate, organically modified montmorillonite clay, hydrated aluminum silicate, fumed silica, carboxyvinyl polymer, sodium carboxymethyl cellulose and ethylene glycol monostearate.

The cosmetically acceptable vehicle, when present, will usually form from 0.01 to 99.9%, preferably from 59 to 98% by weight of the composition, and can, in the absence of other cosmetic adjuncts, form the balance of the composition.

A wide variety of conventional sunscreening agents, such as those described in U.S. Pat. No. 4,919,934 to Deckner et al. hereby incorporated by reference, may also be used in the cosmetic compositions of the invention.

Such agents include, for example, p-aminobenzoic acid, its salts and its derivatives, anthranilates, salicylates, cinnamic acid derivatives, di- and trihydroxy cinnamic acid derivatives, hydrocarbons such as diphenylbutadiene and stilbene, dibenzalacetone and benzalacetophenone, naphthasulfonates, dihydroxy naphthloic acid and its salts, hydroxy diphenylsulfonates, coumarin derivatives, diazoles, quinine salts quinoline derivatives, hydroxy or methoxy substituted benzophenones, uric or vilouric acid, tannic acid and its derivatives, hydroquinone, and benzophenones.

In a sixth embodiment of the invention, the glycosylamides of the invention may be used in a light duty liquid detergent composition such as those taught in U.S. Pat. No. 4,671,894 to Lamb et al, U.S. Pat. No. 4,368,146 to Aronson et al., and U.S. Pat. No. 4,555,360 to Bissett et al., all of which are hereby incorporated by reference into the subject application.

Generally such compositions comprise a mixture of sulphate and sulphonate anionic surfactants together with a suds stabilizing agent. These compositions may also comprise nonionic surfactants designed to reduce the level of non-performing ingredients such as solvents and hydrotropes and zwitterionic surfactants for providing enhanced grease and particulate soil removal performance.

Among other ingredients which may also be used in such compositions are opacifiers (e.g. ethylene glycol distearate), thickeners (e.g., guar gum), antibacterial agents, antitarnish agents, heavy metal chelators (e.g. ETDA), perfumes and dyes.

In an seventh embodiment of the invention the glycosylamides of the invention may be used in underarm deodorant/antiperspirant compositions such as those taught in U.S. Pat. No. 4,919,934 to Deckner, U.S. Pat. No. 4,944,937 to McCall and U.S. Pat. No. 4,944,938 to Patini, all of which are hereby incorporate by reference.

Such compositions generally comprise a cosmetic stick (gel or wax) composition which in turn generally comprises one or more liquid base materials (e,g., water, fatty acid and fatty alcohol esters, water-insoluble ethers and alcohols, polyorganosiloxanes); a solidifying agent for solidifying the liquid base; and an active component such as bacteriostats or fungi stats (for antideodorant activity) or astringent metallic salts for antiperspirant activity).

These compositions may also comprise hardeners, strengtheners, emollients, colorants, perfumes, emulsifiers and fillers.

In another embodiment of the invention, the glycosylamide surfactants of the invention may be used in shaving cream or shaving lotion compositions. A typical shaving cream composition is set forth below:

| Ingredient | % by Weight |
| --- | --- |
| Coconut oil or fatty acid | 6–10 |
| Glycosylamide | 0.1–45 |
| Glycerol | 5–15 |
| Potassium hydroxide | 2–6 |
| Sodium hydroxide | 1–3 |
| Vegetable or mineral oil | 1–5 |
| Water | to balance |

A typical brushless shaving cream composition is also set forth below:

| Ingredient | % by Weight |
| --- | --- |
| Glyceryl monostearate | 10–35 |
| Mineral oil | 5–15 |
| Glycosylamide | 0.1–45 |
| Glycerol | 1–10 |
| Water | to balance |

A typical shaving lotion is set forth below

| Ingredient | % by Weight |
| --- | --- |
| Cellulosic alkyl ether | 70–75 |
| Glycerol | 5–10 |
| Glycosylamide | 0.1–5 |
| Mineral Oil | 10–20 |
| Water | to balance |

In yet another embodiment of the invention, the glycosylamide surfactant may be used in shower gel compositions. A typical shower gel composition is set forth below:

| Ingredients | % by Weight |
| --- | --- |
| Sodium cocoyl isethionate | 5–10 |
| Sodium ether lauryl sulfate | 2–5 |
| Glycosylamide | 0.1–45 |
| Coconut amidopropyl betaine | 8–15 |
| Ethylene glycol distearate | 4–10 |
| Isopropyl palmitate | 0.5–1 |
| Moisturizing factor | 0.25–0.5 |
| Preservative | 0.05–0.1 |
| Sodium chloride | 3–5 |
| Water | to balance |

While various compositions are described above, these should not be understood to be limiting as to what other personal product compositions may be used since other compositions which may be known to those of ordinary skill in the art are also contemplated by this invention.

In addition, the surfactants of the invention may also be used in cleansing or detergent compositions such as heavy duty liquids or detergent powders. Examples of liquid detergent compositions are described in U.S. Pat. No. 4,959,179 to Aronson et al. and examples of powdered detergent compositions are described in U.S. Pat. No. 4,929,379 to Oldenburg et al. Both these patents are hereby incorporated by reference into the subject application.

The liquid detergent compositions of the invention may be built or unbuilt and may be aqueous or nonaqueous. The compositions generally comprise about 5 to 70% by weight of a detergent active material and from 0% to 50% of a builder. The glycosylamide of the invention may be the sole surfactant in the formulation or it maybe a cosurfactant in which it is used in combination with a surfactant selected from the group consisting of soap, anionics, nonionics, cationics and zwitterionic surfactants. If used as a cosurfactant, the glycosylamide may comprise 5 to 99% preferably 5 to 50% of the active system. The liquid detergent compositions of the invention may further comprise an amount of electrolyte (defined as any water-soluble salt) whose quantity depends on whether or not the composition is structured. By structured is meant the formation of a lamellar phase sufficient to endow solid suspending capability.

More particularly, while no electrolyte is required for non-structured, non-suspending composition, at least 1%, more preferably at least 5% by weight and most preferably at least 15% by weight electrolyte is used. The formation of a lamellar phase can be detected by means well known to those skilled in the art.

The water-soluble electrolyte salt may be a detergency builder, such as the inorganic salt sodium tripolyphosphate or it may be a non-functional electrolyte such as sodium sulphate or chloride. Preferably, whatever builder is used in the composition comprises all or part of the electrolyte.

The liquid detergent composition generally further comprises enzymes such as proteases, lipases, amylases and cellulases which, when present, may be used in amounts from about 0.01 to 5% of the compositions. Stabilizers or stabilizer system may be used in conjunction with enzymes and generally comprise from about 0.1 to 15% by weight of the composition.

The enzyme stabilization system may comprise calcium ion boric acid, propylene glycol and/or short chain carboxylic acids. The composition preferably contains from about 0.01 to about 50, preferably from about 0.1 to about 30, more preferably from about 1 to about 20 millimoles of calcium ion per liter.

When calcium ion is used, the level of calcium ion should be selected so that there is always some minimum level available for the enzyme after allowing for complexation with builders, etc., in the composition. Any water-soluble calcium salt can be used as the source of calcium ion, including calcium chloride, calcium formate, calcium acetate and calcium propionate. Small amount of calcium ion, mineral from about 0.05 to about 2.5 millimoles per liter, is often also present in the composition due to calcium in the enzyme slurry and formula water.

Another enzyme stabilizer which may be used is propionic acid or a propionic acid salt capable of forming propionic acid. When used, this stabilizer may be used in an amount from about 0.1% to about 15% by weight of the composition.

Another preferred enzyme stabilizer is polyols containing only carbon, hydrogen and oxygen atoms. They preferably contain from 2 to 6 carbon atoms and from 2 to 6 hydroxy groups.

Examples include propylene glycol (especially 1,2-propanediol which is preferred), ethylene glycol, glycerol, sorbitol, mannitol and glucose. The polyol generally represents from about 0.5% to about 15%, preferably from about 1.0% to about 8% by weight of the composition.

The composition herein may also optionally contain from about 0.25% to about 5%, most preferably from about 0.5% to about 3% by weight of boric acid. The boric acid may be, but is preferably not, formed by a compound capable of forming boric acid in the composition. Boric acid is preferred, although other compounds such as boric oxide, borax and other alkali metal borates (e.g. sodium ortho-, meta- and pyroborate and sodium pentaborate) are suitable. Substituted boric acids (e.g., phenyl boronic acid, butane boronic acid and a p-bromophenyl boronic acid) can also be used in place of boric acid.

One especially preferred stabilization system is a polyol in combination with boric acid. Preferably, the weight ratio of polyol to boric acid added is at least 1, more preferably at least about 1.3.

With regard to the detergent active, the detergent active material may be an alkali metal or alkanolamine soap or a 10 to 24 carbon atom fatty acid, including polymerized fatty acids, or an anionic, a nonionic, cationic, zwitterionic or amphoteric synthetic detergent material, or mixtures of any of these.

Examples of the anionic synthetic detergents are salts (including sodium, potassium, ammonium and substituted ammonium salts) such as mono-, di- and triethanolamine salts of 9 to 20 carbon alkylbenzenesulphonates, 8 to 22 carbon primary or secondary alkanesulphonates, 8 to 24 carbon olefinsulphonates, sulphonated polycarboxylic acids prepared by sulphonation of the pyrolyzed product of alkaline earth metal citrates, (e.g., as described in British Patent specification, 1,082,179), 8 to 22 carbon alkylsulphates, 8 to 24 carbon alkylpolyglycolethersulphates, -carboxylates and -phosphates (containing up to 10 moles of ethylene oxide); further examples are described in "Surface Active Agents and Detergents" (Vol, I and II) by Schwartz, Ferry and Bergh. Any suitable anionic may be used an the examples are not intended to be limiting in any way.

Examples of nonionic synthetic detergents which may be used with the invention are the condensation products of ethylene oxide, propylene oxide and/or battalion oxide with 8 to 18 carbo alkylphenols, 8 to 18 carbon fatty acid amides; further examples of nonionics include tertiary amine oxides with 8 to 18 carbon alkyl chain and two 1 to 3 carbon alkyl chains. The above reference also describes further examples of nonionics.

The average number of moles of ethylene oxide and/or propylene oxide present in the above nonionics varies from 1–30 mixtures of various nonionics, including mixtures of nonionics with a lower and a higher degree of alkoxylation, may also be suitable.

Examples of cationic detergents which may be used are the quaternary ammonium compounds such as alkyldimethylammonium halogens.

Examples of amphoteric or zwitterionic detergents which may be used with the invention are N-alkylamine acids, sulphobetaines, condensation products of fatty acids with protein hydrolysates; but owing to their relatively high costs they are usually used in combination with an anionic or a nonionic detergent. Mixtures of the various types of active detergents ma also be used, and preference is given to mixtures of an anionic and a nonionic detergent active. Soaps (in the form of their sodium, potassium and substituted ammonium salts) of fatty acids may also be used, preferably in conjunction with an anionic and/or nonionic synthetic detergent.

Builders which can be used according to this invention include conventional alkaline detergency builders, inorganic or organic, which can be used at levels from 0% to about 50% by weight of the composition, preferably from 1% to about 20% by weight, most preferably from 2% to about 8%.

Examples of suitable inorganic alkaline detergency builders are water-soluble alkalimetal phosphates, polyphosphates, borates, silicates and also carbonates. Specific examples of such salts are sodium and potassium triphosphates, pyrophosphates, orthophosphates, hexametaphosphates, tetraborates, silicates and carbonates.

Examples of suitable organic alkaline detergency builder salts are: (1) water-soluble amino polycarboxylates, e.g., sodium and potassium ethylenediaminetetraacetates, nitrilotriacetates an N-(2-hydroxyethyl)nitrilodiacetates; (2) water-soluble salts of phytic acid, e.g., sodium and potassium phytates (see U.S. Pat. No. 2,379,942); (3) water-soluble polyphosphonates, including specifically, sodium, potassium and lithium salts of ethane-1-hydroxy-1,1-diphosphonic acid; sodium, potassium and lithium salts of methylene diphosphonic acid; and sodium, potassium and lithium salts of ethane-1,1,2-tri-phosphonic acid.

Other examples include the alkali metal salts of ethane-2-carboxy-1,1-diphosphonic acid hydroxymethanediphosphonic acid, carboxylidiphosphonic acid, ethane-1-hydroxy-1,1,2-triphosphonic acid, ethane-2-hydroxy-1,1,2-triphosphonic acid, propane-1,1,3,3-tetraphosphonic acid, propane-1,1,2,3-tetraphosphonic acid, and propane-1,2,2,3-tetraphosphonic acid; (4) water soluble salts of polycarboxylate polymers and copolymers as described in U.S. Pat. No. 3,308,067.

In addition, polycarboxylate builders can be used satisfactorily, including water-soluble salts of mellitic acid, citric acid, and carboxymethyloxysuccinic acid and salts of polymers of itaconic acid and maleic acid. Other polycarboxylate builders include DPA (dipicolinic acid) and ODS (oxydisuccinic acid). Certain zeolites or aluminosilicates can be used. One such aluminosilicate which is useful in the compositions of the invention is an amorphous water-insoluble hydrated compound of the formula $Na_x(_yAlO_2SiO_2)$, wherein x is a number from 1.0 to 1.2 an y is 1, said amorphous material being further characterized by a Mg++ exchange capacity of from about 50 mg eq. $CaCo_3$/g, and a particle diameter of from about 0.01 micron to about 5 microns. This ion exchange builder is more fully described in British Pat. No. 1,470,250.

A second water-insoluble synthetic aluminosilicate ion exchange material useful herein is crystalline in nature and has the formula $Na_z[(AlO_2)_y(SiO_2)]xH_2O$ wherein z and y are integer of at least 6; the molar ratio of z and y is in the range from 1.0 to about 0.5, and x is an integer from about 15 to about 264; said aluminosilicate ion exchange material having a particle size diameter from about 0.1 micron to about 100 microns; a calcium ion exchange capacity on an anhydrous basis of at least about 200 milligrams equivalent of $CaCO_3$ hardness per gram; and a calcium exchange rate on an anhydrous basis of at least about 2 grams/gallon/minute/gram. These synthetic aluminosilicates are more fully described in British Pat. No. 1,429,143.

In addition to the ingredients described hereinbefore, the preferred compositions herein frequently contain a series of optional ingredients which are used for the known functionality conventional levels. While the detergent compositions are generally premised on aqueous, enzyme-containing detergent compositions, it is frequently desirable to use a phase regulant. This component together with water constitutes then the solvent matrix for the claimed liquid compositions. Suitable phase regulants are well-known in liquid detergent technology and, for example, can be represented by hydrotropes such as salts of alkylarylsulfonates having up to 3 carbon atoms in the alkyl group, i.e., sodium potassium ammonium and ethanolamine salts of xylene-, toluene-, ethylbenzene-, cumene-, and isopropylbenzene sulfonic acids. Alcohols may also be used as phase regulants. This phase regulant is frequently used in an amount from about 0.5% to about 20%. The sum of phase regulant and water is normally in the range from 35% to 65%.

The preferred compositions herein can contain a series of further optional ingredients which are mostly used in additive levels, usually below about 5%. Examples of the like additives include: polyacids, suds regulants, opacifiers, antioxidants, bactericides, dyes, perfumes, brighteners and the like.

The beneficial utilization of the claimed compositions under various usage conditions can require the utilization of a suds regulant. While generally all detergent suds regulants can be utilized, preferred for use herein are alkylated polysiloxane such as dimethylpolysiloxane, also frequently termed silicones. The silicones are frequently used in a level not exceeding 0.5%, most preferably between 0.01% and 0.2%.

It can also be desirable to utilize opacifiers in as much as they contribute to create a uniform appearance of the concentrated liquid detergent compositions. Examples of suitable opacifiers include: polystyrene commercially known as LYTRON 621 manufactured by Monsanto Chemical Corporation. The opacifiers ar frequently used in an amount from 0.3% to 1.5%.

The compositions herein can also contain known antioxidants for their known utility, frequently radical scavengers in the art established levels, i.e., 0.001% to 0.25% (by reference to total composition). These antioxidants are frequently introduced in conjunction with fatty acids.

The liquid detergent compositions of the invention may also contain deflocculating polymers such as described in U.S. Pat. No. 5,147,576 to Montague et al., hereby incorporated by reference.

When the liquid composition is an aqueous composition the balance of the formulation consists of an aqueous medium. When it is in the form of a non-aqueous composition, the above ingredients make up for the whole formulation (a non-aqueous composition may contain up to about 5% water).

An ideal liquid detergent composition might contain (all percentages by weight):

(1) 1–70% detergent active (or active mixture);
(2) 0.1–60% glycosylamide;
(3) 0–50% builder;
(4) 0–40% electrolyte
(5) 0.01–5% enzyme;
(6) 0.1–15% enzyme stabilizer;
(7) 0–20% phase regulant; and
(8) remainder water and minors The detergent composition of the invention might also be a powdered detergent composition.

Such powdered compositions generally comprise from about 5–40% of a detergent active system which generally consists of an anionic, a nonionic active, a fatty acid soap or mixtures thereof from 20–70% of an alkaline buffering agent; up to about 40% builder and balance minors and water.

The alkaline buffering agent may be any such agent capable of providing a 1% product solution with a pH of 8 or above, preferably above 11 or even 12. Advantageous alkaline buffering agents are the alkalimetal silicates, as they decrease the corrosion of metal parts in washing machines, and in particular sodium orthometa- or di-silicates, of which sodium metasilicate is preferred. The alkaline buffering agent is present in an amount of from 0 to 70% by weight preferably from 0 to 30% by weight.

In addition the compositions of the invention can and normally will contain detergency builders in an amount of up to 40% by weight and preferably from 5 to 25% by weight of the total composition.

Suitable builders include sodium, potassium and ammonium or substituted ammonium pyro- and tripolyphosphates, -ethylenediamine tetraacetates, -nitrilotriacetates, -etherpolycarboxylates, -citrates, -carbonates, -orthophosphates, -carboxymethyloxysuccinates, etc. Other builders include DPA and ODS. Also less soluble builders may be included such as e.g., easily dispersible zeolite. Particularly preferred are the polyphosphate builder salts, nitrilotriacetates, citrates, carboxymethyloxysuccinates and mixtures thereof.

Other conventional materials may be present in minor amounts, provided they exhibit a good dissolving or dispersing behavior; for example sequestering agents, such as ethylenediamine tetraphosphonic acid; soil-suspending agents, such as sodium carboxymethylcellulose, polyvinylpyrrolidone or the maleic anhydride/vinylmethylether copolymer, hydrotropes; dyes; perfumes; optical brighteners; alkali-stable enzymes; germicides; anti-tarnishing agents; lather depressants; fabric softening agents; oxygen- or chlorine-liberating bleaches, such as dichlorocy anuric acid salts or alkali metal hypochlorides.

The remainder of the composition is generally water, which may be present at least in part as bound water of hydration, such as e.g., in the form of silicate 5 moles of water.

An ideal powdered detergent composition might contain the following (all percentages by weight):

(1) 1–50% detergent active (or active mixture);
(2) 0.1–60% glycosylamide;
(3) 0–40% builder;
(4) 0–30% buffer salt;
(5) 0–30% sulfate;
(6) 0–20% bleach system;
(7) 0–4% enzyme;
(8) minors plus water to 100%.

Many additional essential and optional ingredients that are useful in the detergent and personal product compositions of the present invention are those described in McCutcheon's, Detergents and Emulsifiers (Vol. 1) and McCutcheon's, Functional Materials (Vol. 2), 1995 Annual Edition, published by McCutcheon's MC Publishing Co., as well as the CTFA (Cosmetic, Toiletry and fragrance Associations) 1992 International buyers Guide, published by CFTA Publications and OPD 1993 Chemicals Buyers directory 80th Annual Edition, published by Schnell Publishing Co., Cosmetic and Toiletry Formulations Vol 1–4, Advanced Cleaning Product Formulations Vol. 1–2, and Industrial Surfactants all of which are incorporated in full herein by reference.

Method of Manufacture of Glycosylamides

In another embodiment of the invention, a new and improved process for the manufacture of alkyl glycosylamides surfactants has now been found. It has been found, in accordance with the present invention, that glycosylamide surfactants may be readily prepared by reacting glycosylamines with alkyl anhydrides or mixed anhydrides at room temperature in the presence an organic solvent.

The method is especially suitable for the manufacture of alkyl glycosylamides of the general formula:

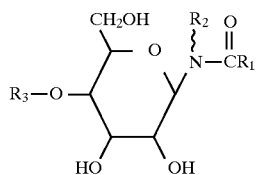

wherein $R_1$, $R_2$ and $R_3$ are described previously.

Examples of glycosylamines suitable for this method include but are not limited to glucosylamine, maltosylamine, lactosylamine, galactosylamine, methyl glucosylamine, methyl maltosylamine, methyl lactosylamine, methyloxypropyl glucosylamine, coconut maltosylamine, oleyl glucosylamine and the like.

Examples of linear alkyl anhydrides (linear acid anhydrides) suitable for this method include, but are not limited to acetic anhydride, propionic anhydride, butyric anhydride, valeric anhydride, caproic anhydride, enanthic anhydride, caprylic anhydride, pelargonic anhydride, capric anhydride, lauric anhydride, myristic anhydride, palmitic anhydride, stearic anhydride, oleic anhydride, linoleic anhydride, docosanoic anhydride, isobutyric anhydride, 2-methylbutyric anhydride, isobutenyl anhydride, trimethylacetic anhydride, crotonic anhydride, methacrylic anhydride, chloroacetic anhydride, trichloroacetic anhydride, trifluoroacetic anhydride, pentafluoropropionic anhydride, heptafluorobutyric anhydride; cyclic anhydrides (cyclic acid anhydrides) such as glutaric anhydride, 3-methylglutaric anhydride, 2,2-dimethylglutaric anhydride, 3,3-dimethylglutaric anhydride, 3-ethyl-3-methylglutaric anhydride, hexafluoroglutaric anhydride, succinic anhydride, methylsuccinic anhydride, 2,2-dimethylsuccinic anhydride, isobutenylsuccinic anhydride, S-acetylmercaptosuccinic anhydride, $C_2$–$C_{18}$ alkylsuccinic anhydride, $C_2$–$C_{18}$ alkylenesuccinic anhydride, $C_1$–$C_{18}$ alkyloxypolyoxyethylenesuccinic anhydride, 3,5-diacetyltetrahydropyran-2,4,6-anhydride, phthalic anhydride, hexahydro-4-methylphthalic anhydride, cis-1,2,3,6-tetrahydrophthalic anhydride, 3,4,5,6-tetrahydrophthalic anhydride, 4-methylphthalic anhydride, 3,6-difluorophthalic anhydride, 3,6-dichlorophthalic anhydride, 4,5-dichlorophthalic anhydride, 3-hydroxyphthalic anhydride, 4-nitrophthalic anhydride, maleic anhydride, 2,3-dimethylmaleic S-acetylmercaptosuccinic anhydride, citrconic anhydride, itaconic anhydride, cis 1,2-cyclohexane dicarboxylic acid anhydride, trans 1,2-cyclo-hexane dicarboxylic anhydride, 1-cyclopentene-1,2-dicarboxylic anhydride, 5-norbornene-2,3-dicarboxylic anhydride; and mixed alkyl anhydrides (carbonate carboxylic acid anhydrides or formate carboxylic acid anhydrides) such as ethyl hydrogen carbonate acetic anhydride, propyl hydrogen carbonate acetic anhydride, butyl hydrogen carbonate propionic anhydride, isobutyl hydrogen carbonate butyric anhydride, ethyl hydrogen carbonate valeric anhydride, methyl hydrogen carbonate caproic anhydride, ethyl hydrogen carbonate enanthic anhydride, heptyl hydrogen carbonate caprylic anhydride, ethyl hydrogen carbonate pelargonic anhydride, ethyl hydrogen carbonate capric anhydride, propyl hydrogen carbonate lauric anhydride, ethyl hydrogen carbonate myristic anhydride, ethyl hydrogen carbonate palmitic anhydride, ethyl hydrogen carbonate stearic anhydride, ethyl hydrogen carbonate oleic anhydride, ethyl hydrogen carbonate linoleic anhydride, ethyl hydrogen carbonate docosanoic anhydride, isopropyl hydrogen carbonate isobutyric anhydride, ethyl hydrogen carbonate 2-methylbutyric anhydride, ethyl hydrogen carbonate isobutenyl anhydride, ethyl hydrogen carbonate isotridecyl anhydride, hexyl hydrogen carbonate trifluroacetic anhydride, ethyl hydrogen carbonate pentafluoropropionic anhydride, ethyl hydrogen carbonate heptafluorobutyric anhydride, ethyl hydrogen carbonate $C_1$–$C_{18}$ alkylpolyoxyethylene anhydride, ethyl hydrogen carbonate $C_1$–$C_{18}$ alkylpolyoxypropylene anhydride, ethyl hydrogen carbonate $C_1$–$C_{18}$ alkylpolyoxy ethylenepolyoxypropylene anhydride, butyl hydrogen carbonate acetic anhydride, isobutyl hydrogen carbonate acetic anhydride and the like or mixtures thereof.

When acetic anhydride, triflouroacetic anhydride, ethyl hydrogen carbonate acetic anhydride and the like are used, they may leave in some instances, a residual odor of acetic acid. Often this can be covered up with perfume or prevented by neutralization with base. However, in some applications the presence of residual acetic acid odor is most undesirable. This can be further avoided by using an anhydride having a lower vapor pressure such as propionic anhydride, valeric anhydride, succinic anhydride, maleic anhydride and the like.

The alkyl anhydrides represent a preferred amidating reagent of the invention, however other "activated" fatty acids can be used as well and may be suitable in certain cases. Examples of other activated fatty acids that are known or become known, include but are not limited to, fatty acid halides and the like.

Examples of fatty acid halides, include but are not limited to $C_2$–$C_{18}$ alkyl acid chloride, $C_2$–$C_{18}$ alkyl acid bromide, oleic acid chloride, linoleic acid chloride, coconut acid chloride, soya acid chloride, tallow acid chloride, castor acid chloride, cottonseed acid chloride, palm acid chloride, rapeseed acid chloride, $C_1$–$C_{18}$ alkyl polyoxyethylene acid chloride, $C_1$–$C_{18}$ alkyl polyoxypropylene acid chloride, $C_1$–$C_{18}$ alkyl polyoxypropylenepolyoxyethylene acid chloride and the like.

Within the process of the invention, it is most desirable to use water-free reaction components. Also, within the process of the invention, the glycosylamine can be added progressively to the anhydride, or the anhydride can be added progressively to the glycosylamine, preferably however, both reagents are added in full amount at the beginning of the reaction. The glycosylamine can be used in stoichiometric (equal) molar amounts relative to the anhydride, or the anhydride can be used in molar excess relative to the glycosylamine, preferably however, as seen in Examples #1 through #9, the anhydride is used in molar excess relative to the glycosylamine. The molar excess of anhydride to glycosylamine is from about 10:1 to about 1:10, preferably from about 7:1 to about 1:2, more preferably from about 5:1 to about 1:1.5. The use of excess alkyl anhydride is satisfactory and can drive the reaction to completion.

The glycosylamine or anhydride is preferably in crystalline or liquid form respectively, however solid, flake, paste, gel or granular form can be used as well.

The reaction can be performed at or below room temperature, however shorter reaction times can be achieved at elevated temperature. Favorable reaction temperatures are from about –20° C. to about 80° C., preferably from about –10° C. to about 70° C., most preferably from about 0° C. to about 50° C.

The reaction can be carried out under pressure or reduced pressure to assist in the overall reaction rate, however, it is preferably carried out at atmospheric pressure and under an inert gas blanket such as nitrogen, argon or helium, most preferably it is carried out at atmospheric pressure without an inert gas.

The substrates are reacted with intensive stirring for several hours, preferably from about 0.25 hour to about 96 hours, more preferably from about 0.5 hour to about 48 hours, most preferably when the reaction is complete and is verified by an analytical technique such as thin layer chromatography (TLC), infrared spectroscopy (IR), proton nuclear magnet resonance ($H^1$ NMR), carbon 13 nuclear magnetic resonance ($C^{13}$ NMR), direct chemical ionization mass spectrometry (DCI MS), fast atom bombardment mass spectrometry (FAB MS), high pressure liquid chromatography (HPLC) and the like.

An alkaline neutralizing agent or alkaline catalyst can be optionally used to maintain a neutral pH or to accelerate the rate of the reaction, however these materials are usually not preferred. These materials are generally classified as an organic or inorganic bases and are usually not preferred since bases can accelerate the rate of by-product formation and Amodori rearrangement. Examples of such alkaline neutralizing agents/catalysts that may be useful in the present method include, but are not limited to sodium hydroxide, potassium hydroxide, ammonium hydroxide, calcium hydroxide, magnesium hydroxide, sodium metal, potassium metal, sodium methoxide, potassium methoxide, sodium ethoxide, potassium ethoxide, sodium carbonate, potassium carbonate, ammonium carbonate, magnesium carbonate, calcium carbonate, lithium carbonate, sodium bicarbonate, potassium bicarbonate, ammonium bicarbonate, magnesium bicarbonate, calcium bicarbonate, trisodium phosphate, tripotassium phosphate, tetrasodium pyrophosphate, tetrapotassium pyrophosphate, pentasodium tripolyphosphate, pentapotassium tripolyphosphate, disodium tartrate, dipotassium tartrate, sodium potassium tartrate, trisodium citrate, tripotassium citrate, sodium acetate, potassium acetate, sodium valerate, sodium laurate, potassium laurate, sodium myristate, potassium myristate, sodium stearate, sodium oleate, sodium 12-hydroxydodeconate, sodium 2,2-dimethylbutyrate, disodium oxalate, dipotassium oxalate, disodium malonate, dipotassium malonate, disodium succinate, dipotassium succinate, disodium dodecyl succinate, disodium glutarate, dipotassium glutarate, disodium 1,12-dodecanedicarboxylate, trisodium tricarballylate, tripotassium tricarballylate, tetrasodium 1,2,3,4-butanetetracarboxylate, tetrapotassium 1,2,3,4-butanetetracarboxylate, disodium itaconate, dipotassium itaconate, disodium maleate, dipotassium maleate, disodium fumarate, dipotassium fumarate, disodium malate, disodium agaricate, dipotassium agaricate, sodium ethoxyacetate, sodium glycoxylate, sodium 4-acetylbutyrate, sodium cyclohexylacetate, trisodium 1,3,5-cyclohexanetricarboxylate, sodium basic silicates, potassium basic silicates, sodium basic aluminosilicates, potassium basic aluminosilicates, sodium lactate, potassium lactate, ammonium lactate, sodium glycinate, sodium dimethylglycinate, pentasodium diethylenetriaminepentaacetate (DTPA), tetrasodium ethylenediaminetetraacetate (EDTA), tetrapotassium ethylenediaminetetraacetate, calcium disodium ethylenediaminetetraacetate, triethylamine, tripropylamine, tributylamine, trioctylamine, N,N-dimethyldodecylamine, N,N'-diethylethylenediamine, N,N-diethyl-N'-methylethylenediamine, N,N,N N'-tetramethylethylenediamine, N,N,N',N'-tetra-ethylethylenediamine, N,N,N', N'-tetramethylethylenediamine, N,N,N',N'-tetraethyl-1,3-propanediamine, triethanolamine, diethanolamine, pyridine, morpholine, picoline, collidine, ethylpiperidine diethylcyclohexylamine and the like. Mixtures of base catalysts can be also used as well and may be preferred in certain cases.

When the base is used as a neutralizing agent, it can be added at any time during the reaction, however it is preferably added during the reaction portionwise (to maintain a neutral or alkaline pH) or at the end of the reaction in full amount. The molar ratio of alkyl anhydride (or alkyl acid) to alkaline neutralizing agent is from about 2:1 to about 1:50, preferably from about 1.6:1 to about 1:25, most preferably from about 1.5:1 to about 1:10.

When the base is used as a catalyst, it can be added at any time during the reaction, however it is preferably added at the beginning of the reaction and in full amount. The use of an alkaline catalyst or neutralizing agent can also enhance the rate of esterification of hydroxyl groups on the sugar head group, which are themselves, innocuous and colorless, and so they can remain in the finished product (in low amounts) without need for further purification or in certain cases they may be removed by hydrolysis. The molar ratio of alkyl anhydride to base catalyst is from about 500:1 to about 20:1, preferably from about 300:1 to about 100: 1, most preferably from about 250:1 to about 150:1.

In general, an organic solvent can be used to perform the reaction of the present invention. The quantity of solvent should be sufficient to dissolve the glycosylamine and anhydride, but otherwise this is not an essential condition. Typical levels of solvent used are from about 5% to about 98%, preferably from about 15% to about 75%, most preferably from about 20% to about 65% by weight of the total reaction mixture. Preferably the solvent is removed (after the reaction is complete) by known procedures such as simple distillation, vacuum distillation or rotorary evaporation. However, this may not be feasible when high boiling materials, such as propylene glycol, ethylene glycol, diethylene glycol, polyethylene glycol and the like are used as solvents, or when other useful composition ingredients such as nonionic surfactants, sorbitol and the like, are used as pseudo-solvents or phase transfer agents. These materials are preferably left in the finished product and generally do not present a problem. In fact, in some cases, it may be more beneficial, especially when formulating liquid detergent compositions, where glycosylamide can be pumped directly into the formulation.

When long chain linear acid anhydrides are used as acylating agents, these materials produce (fatty) alkyl acids which may also be left in the finished product and generally do not present a problem. In fact in some cases, these materials can also be more beneficial, since fatty acids can function as processing aids, cleansing agents, surface-active agents, suds suppressing agents (e.g. fatty acid calcium salts), builders, sequestrants and the like.

In general, the glycosylamide surfactants of the present invention are isolated as solids (by gravity filtration, vacuum filtration, centrifugation or other separation techniques), however when syrups are obtained, crystallization may be enhanced by the addition of an organic solvent. The resulting product is subsequently filtered, washed with an organic solvent and air or vacuum dried.

Optionally, purification of (solid) glycosylamide surfactants can be performed by recrystallization in an organic solvent. The amount of solvent used is sufficient to dissolve the product, preferably with heating. The solution is then slowly cooled until recrystallization is complete, subsequently filtered, washed with an organic solvent and air or vacuum dried.

Still optionally, further purification of (solid) glycosylamide surfactants can be performed by washing with an organic solvent. A necessary criteria for washing with an organic solvent, is that the (fatty) alkyl acid be soluble in the organic solvent and the glycosylamide be insoluble in the organic solvent. When this condition is met, the glycosylamide can be washed with sufficient amounts of solvent which can remove the (fatty) alkyl acid by-product. The glycosylamide can be washed manually or washed automatically and continuously by soxhlet extraction. The amount of solvent necessary can be determined by simply experimentation by those skilled in the art.

Still optionally, further purification of glycosylamide surfactants can be performed by column chromatography. A preferred version of this method involves passing a solution of glycosylamide through a column containing an acidic ionic exchange resin which can capture the unreacted glycosylamide or alkyl amine, followed by passing through a column containing a basic ionic exchange resin which can capture the (fatty) alkyl acid by-product obtained form the alkyl anhydride. Water or solvent is used to assist in the removal of the glycosylamide from the column to provide an eluate. If water is used, it may be left in, or partially removed from the eluate. If a solvent is used, it may be partially or completely removed from the eluate by simple distillation, vacuum distillation or rotaevaporation. If the product precipitates out of solution during solvent removal, it is preferably filtered, washed with an organic solvent and air or vacuum dried. The substrates left on the ionic exchange resin can be recovered by washing the resin with an appropriate solution of base or acid, which are then separated, optionally purified and recycled. Similar methods of purification are described in U.S. Pat. Nos. 5,296,588 and 5,336,765 to Au et al. which are both incorporated herein by reference.

Typical examples of ionic exchange resin useful for ionic exchange chromatography include, but are not limited to Amberlite CG-50, Amberlite CG-420, Amberlite IR-118, Amberlite IR-120, Amberlite IR-120 (Plus), Amberlite IRA-68, Amberlite IRA-400, Amberlite IRA-410, Amberlite IRA-743, Amberlite IRA-900, Amberlite IRA-904, Amberlite IRC-50S, Amberlite IRC-718, Amberlite IRP-64, Amberlite IRP-69, Amberlite MB-3A, Amberlyst 15, Amberlyst A-21, Amberlyst A-26, Amberlyst A-27, Amberlyst XN-1010, Dowex 1X2-100, Dowex 1X2-200, Dowex 1X2-400, Dowex 1X8-100, Dowex 1X8-200, Dowex 1X8-400, Dowex 50WX2-100, Dowex 50WX2-50WX2-400, Dowex 50WX4-200 Dowex 50WX4–400, Dowex 50WX8-100, Dowex 50WX8-200, Dowex 50WX8-400 and the like.

Still optionally, further purification of glycosylamide surfactants can also be performed by extraction from a mixture of water and organic solvent. A necessary criteria for extraction is that the organic solvent be immiscible with water. Preferably the glycosylamide surfactant should be soluble in water and the alkyl anhydride and (fatty) alkyl acid should be soluble in the solvent, however this is not a necessary condition. The alkyl anhydride and (fatty) alkyl acid are then extracted into the solvent layer and removed from the aqueous layer containing the glycosylamide surfactant. The water and organic layers are separated from each other, the solvent is removed, and the components in that solvent layer can be purified or recyclized. A mild vacuum is applied to the aqueous layer, removing any trace solvents, and the water is left with the final product free of alkyl acid and alkyl anhydride.

Typical reaction solvents, crystallization solvents, recrystallization solvents, washing solvents and eluting solvents that may be used include, but are not limited to acetic acid, acetone, acetonitrile, butanol, sec-butanol, tertbutanol, butyl acetate, butyl chloride, chloroform, cyclohexane, cyclopentane, dimethylformamide (DMF), dimethylacetamide, dimethylsulfoxide (DMSO), 2-ethoxyethanol, ethyl acetate, ethyl ether, ethylene glycol dimethyl ether (glyme), pentane, hexane, heptane, hexadecane, methanol, 2-methoxyethanol, 2-methoxyethyl acetate, methylethylketone (MEK), methylisoamylketone, methylisobutylketone, butylmethylketone, diisobutylketone, N-methyl-2-pyrrolidone, petroleum ether, propanol, isopropanol, propylene carbonate, pyridine, tetrachloroethylene, tetrahydrofuran (THF), tetramethylurea, toluene, trichloroethylene, 1,2,2-trichloro-1,2,2-trifluoroethane, 2,2,4-trimethylpentane, xylene, ethanol, pentyl acetate, carbon disulfide, 1-chlorobutane, 1,2-dichloroethane, 1,2-dimethoxyethane, glycerol, methylcyclohexane, ethylene glycol, furan, 1,2-dimethoxyethane, propylene glycol (1,2-propanediol), 1-chloro-1,1-difluoroethane, isopropyl-benzene (cumene), cyclohexanol, cyclohexanone, 4-hydroxy-4-methyl-2-pentanone (diacetone alcohol), diethylene glycol, diisopropyl ether, ethylene glycol monobutyl ether (2-butoxyethanol), ethylene glycol monomethyl ether (2-methoxyethanol), hexylene glycol, isopentyl acetate, isobutyl acetate, isopropyl acetate, methyl acetate, methylpentylketone and the like, however, alcohols are the preferred reaction solvents and acetone, acetates or alcohols are the preferred recrystallization/washing solvents. Mixtures of solvents can be used as well and may be preferred in certain cases. Mixtures of solvents are useful in obtaining a desired polarity which may not be easily achieved through use of individual solvents.

Optionally, the reaction may also be carried out in the presence of phase transfer agent, such as a typical ethoxylated/propoxylated surfactant useful as phase transfer agents are described in McCutcheon's, Detergents and Emulsifiers (Vol 1), 1993 North American Edition and McCutcheon's, Detergents and Emulsifiers (Vol 1), 1993 International Edition, published by McCutcheon's MC Publishing Co. which are both incorporated herein by reference.

When an organic solvent is used, the reaction can be done in the absence or presence of alkaline catalyst which is used to accelerate the rate of the reaction. When the reaction is complete, the alkaline catalyst may be optionally neutralized with an organic or inorganic acid, however this may not be a necessary condition since the by-product from the anhydride is usually a (fatty) alkyl acid compound.

The neutralized (fatty) alkyl acid (usually a salt compound), is innocuous and can remain in the finished product. This mixture is suitable for formulation without further purification.

Examples of suitable neutralizing acids include, but are not limited to hydrochloric acid, sulfuric acid, phosphoric acid, boric acid, nitric acid, oxalic acid, malonic acid, glutaric acid, adipic acid, sebacic acid, tricarballylic acid, 1,2,3,4-butanetetracarboxylic acid, itaconic acid, maleic acid, malic acid, fumaric acid, citraconic acid, glutaconic acid, bis(hydroxymethyl)propionic acid, tartaric acid, citric acid, formic acid, lactic acid, acetic acid, benzoic acid, gluconic acid, glucoheptonic acid, lactobionic acid, maltobionic acid, coconut fatty acid, lauric acid, myristic acid, palmitic acid, valeric acid, 2-propylpentanoic acid, succinic acid, dodecenyl succinic acid, arotonic crotonic acid, tiglic acid, glycolic acid, ketomalonic acid, methoxyacetic acid, ethoxyacetic acid, 3-methoxypropionic acid, 6-nitrocaproic acid, levulinic acid, chelidonic acid, cyclobutanecarboxylic acid, 1,1-cyclohexanediacetic acid, glycine, phenylacetic acid, 3-benzoylpropionic acid, S-benzylthioglycolic acid, phenylmalonic acid, 2-hydroxyphenylacetic acid, toluene-sulfonic acid, S-sulfobenzoic acid, 5-sulfoisophthalic acid, dodecylbenzenesulfonic acid, methanesulfonic acid, ethanesulfonic acid, propanesulfonic acid, dodecylsulfonic acid, 3-hydroxy-1-propanesulfonic acid, isethionic acid, ionic exchange resin and the like. Mixtures of acids can be used as well. Preferred neutralizing acids include hydrochloric acid, oxalic acid, tartaric acid, citric acid, formic acid, lactic acid, dodecylbenzenesulfonic acid and methanesulfonic acid. The amount of neutralizing acid used will be that which is sufficient to provide a pH in the range of about 4 to about 9, preferably from about 5 to about 8, most preferably about 7. Neutralization may be done in water or in an inert organic solvent or mixtures thereof at about 0° C. to about 35° C.

It has been found in accordance to the present invention that improved yields and purity of glycosylamides can be obtained by performing the reaction in the presence of drying agent. It is known that water has a detrimental effect on the glycosylamine substrate causing the reaction to revert back to starting materials. Therefore, it is important to remove the water of reaction and shift the equilibrium towards the glycosylamine substrate. This is more easily understood when reference is made to the general equation:

tetrahydrate, oxone, t-butyl hydro-peroxide, benzoyl peroxide, bis(trimethylsilyl)peroxide, peroxymonosulfate, peroxyformic acid, peroxyacetic acid, peroxytrifluoroacetic acid, peroxybenzoic acid, m-chloroperoxybenzoic acid, peroxyphthalic acid, peroxymaleic acid, peroxypropionic acid, peroxylauric acid and the like. However, hydrogen peroxide and hydrogen peroxide liberating or generating compounds are preferred. Bleaching may be optionally done in water, in an inert organic solvent or mixtures thereof, before or during the reaction or after the reaction is complete, preferably however, bleaching is done after the reaction is complete at about 0° C. to about 75° C. in water or in an aqueous organic solvent system. Typical levels of bleaching agent are from about 0.01% to about 7%, preferably from about 0.02% to about 5%, even more preferably from about 0.03% to about 3% by weight of the total reaction mixture.

Color improvement may also be carried out by using reducing agents belonging to two classes.

The first class of agents comprises compounds which include sulfur in the +4 oxidation state and show a negative oxidation relative to hydrogen. Illustrative of this class are salts of sulfite, bisulfite, hydrosulfite (dithionite), metabisul-

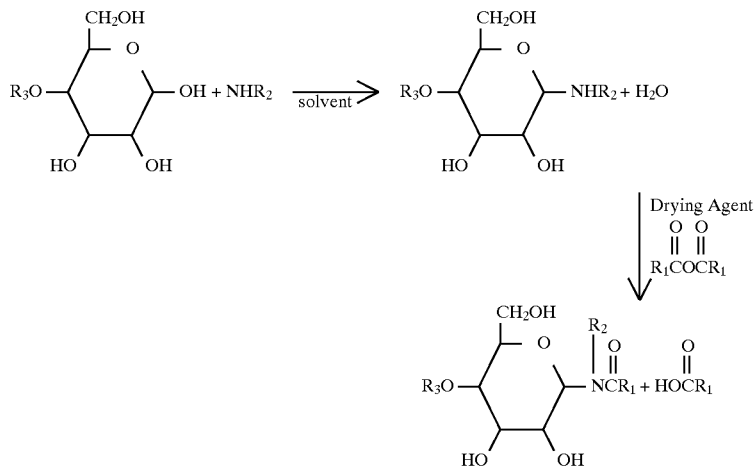

Examples of drying agents useful in removing water from the reaction include but is not limited to sodium carbonate, calcium carbonate anhydrous calcium chloride, anhydrous zinc chloride, anhydrous calcium sulfate, silica gel, calcium oxide, calcium hydroxide, sodium sulfate, magnesium sulfate, magnesium chloride, calcium hydride, sodium hydride and the like. Any drying agent known in the art can be used as long as the agent does not react or cause any unwanted side reactions with the glycosylamine, sugar anhydride or amine. The drying agent useful should only react with water. Typical levels of drying agent are from about 0.01% to about 50%, preferably from about 0.02% to about 40%, even more preferably from about 0.03% to about 30% by weight of the total reaction mixture.

Bleaching is sometimes required but not always necessary, since the compounds of the invention are generally of good color. Bleaching agents or peroxy compounds that may be used to further improve product color are hydrogen peroxide, sodium hypochlorite, potassium hypochlorite, calcium hypochlorite, lithium hypochlorite, dibasic magnesium hypochlorite, sodium hypobromite, chlorinated trisodium phosphate, hypochlorous acid, chlorine dioxide, sodium percarbonate, potassium percarbonate, sodium perborate monohydrate, sodium perborate fate (pyrosulfite) and mixtures thereof. Suitable salt counter ions include alkali metal, alkaline earth metal, ammonium, alkyl- or hydroxyalkylammonium cations and mixtures thereof. Specific examples include, but are not limited to sodium sulfite, potassium sulfite, calcium sulfite, sodium bisulfite (sodium hydrogen sulfite), potassium bisulfite, sodium hydrosulfite, zinc hydrosulfite, sodium metabisulfite and potassium metabisulfite. Sulfur dioxide, sulfurous acid and sodium sulfoxylate formaldehyde are useful as well.

The second class of reducing agents includes those compounds having hydrogen in the −1 oxidation state and show a negative oxidation potential relative to hydrogen. Illustrative of this class are sodium hydride, potassium hydride, calcium hydride, lithium hydride, magnesium hydride, sodium borohydride, sodium cyano borohydride, potassium borohydride, lithium borohydride, magnesium borohydride, alkyl- and alkoxy borohydrides, aluminum hydride, sodium aluminum hydride, potassium aluminum hydride, calcium aluminum hydride, lithium aluminum hydride, alkyl- and alkoxy aluminum hydrides such as sodium dihydrobis(2-methoxyethoxy)aluminate, diboranes and mixtures thereof. Particularly preferred among the foregoing are the bisulfites and borohydrides, most especially preferred are sodium bisulfite and sodium borohydride and mixtures thereof.

Reduction may be optionally done in water or in an inert organic solvent before or during the reaction or after the reaction is complete, preferably however, reduction is done without water or an organic solvent and after the reaction is complete at about 0° C. to about 100° C. Typical levels of reducing agent are from about 0.01 % to about 7%, preferably from about 0.02% to about 5%, even more preferably from about 0.03% to about 3% by weight of the total reaction mixture.

The glycosylamide surfactants prepared by the method of the invention are generally isolated as crystalline solids in good yield, high purity and desirable color.

Home Application and Use

The glycosylamide surfactants are useful in a variety of detergent, personal product, cosmetic, oral hygiene, food, pharmacological and industrial compositions which are available in many types and forms. Preferred compositions, however, are detergent and personal product compositions.

A classification according to detergent type would consist of heavy-duty detergent powders, heavy duty detergent liquids, light duty liquids (dishwashing liquids), machine dishwashing detergents, institutional detergents, specialty detergent powders, specialty detergent liquids, laundry aids, pretreatment aids, after treatment aids, presoaking products, hard surface cleaners, carpet cleansers, carwash products and the like.

A classification according to personal product type would consist of hair care products, bath products, cleansing products, skin care products, shaving products and deodorant/antiperspirant products.

Examples of hair care products include, but are not limited to rinses, conditioners, shampoos, conditioning shampoos, antidandruff shampoos, antilice shampoos, coloring shampoos, curl maintenance shampoos, baby shampoos, herbal shampoos, hair loss prevention shampoos, hair growth/promoting/stimulating shampoos, hairwave neutralizing shampoos, hair setting products, hair sprays, hair styling products, permanent wave products, hair straightening/relaxing products, mousses, hair lotions, hair tonics, hair pomade products, brillantines and the like.

Examples of bath products include, but are not limited to bath oils, foam or bubble bathes, therapeutic bathes, after bath products, after bath splash products and the like.

Examples of cleansing products include, but are not limited to shower cleansers, shower gels, body shampoos, hand/body/facial cleansers, abrasive scrub cleansing products, astringent cleansers, makeup cleansers, liquid soaps, toilet soap bars, synthetic detergent bars and the like.

Examples of skin care products include, but are not limited to hand/body/facial lotions, sunscreen products, tanning products, self-tanning products, aftersun products, masking products, lipsticks, lip gloss products, rejuvenating products, antiaging products, antiwrinkle products, anticellulite products, antiacne products and the like.

Examples of shaving products include, but are not limited to shaving creams, aftershave products, preshave products and the like.

Examples of deodorant/antiperspirant products include, but are not limited to deodorant products, antiperspirant products and the like.

A classification according to oral hygiene type would consist of, but is not limited to mouthwashes, pre-brushing dental rinses, post-brushing rinses, dental sprays, dental creams, toothpastes, toothpaste gels, tooth powders, dental cleansers, dental flosses, chewing gums, lozenges and the like.

The glycosylamide surfactants of the present invention are also useful in softening compositions such as liquid fabric softeners, fabric softening rinses, fabric softening sheets, tissue papers, paper towels, facial tissues, sanitary tissues, toilet paper and the like.

A classification according to composition form would consist of aerosols, liquids, gels, creams, lotions, sprays, pastes, roll-on, stick, tablet, powdered and bar form.

Industrial Application and Use

The glycosylamide surfactants of the present invention are useful as mild nonionic surfactants that may be used alone or in combination with other surfactants to provide low foam and clarity. More specifically, the glycosylamide surfactants of the invention are useful as sole surfactants, cosurfactants, detergents, detergency enhancing agents, soil release agents, pearlescent agents (opacifiers), foaming agents, foam modifying agents, suspending agents, emulsifying agents, wetting agents, solubilizing agents, clarifying agents, lime soap dispersants, anti-hygroscopic agents, bleach stabilizing agents, flow agents, processing aids, viscosity enhancement agents, thickening agents, softening agents, moisturizers, emollients, skin (cell) proliferation agents, enzyme stabilizing agents, gel agents, deposition agents, and the like. In fact, by simple experimentation, which are well known to those skilled in the art, unique synergies of glycosylamide surfactants with essential and optional ingredients can be obtained and determined.

The following Examples further describe and demonstrate the preferred embodiments that are within the scope of the present invention. The Examples are given solely for the purpose of illustration and are not to be construed as being limiting to the present invention since may variations are possible without departing from the spirit and scope of the invention.

EXAMPLE 1

Preparation of N-Acetyl-N-Dodecyl D-Maltosylamine in the Absence of a Drying Agent Maltose (10 g), dodecylamine (5.2 g, 1 eq) were added to methanol (100 ml) at 40°–50° C. for 16 hours. Acetic anhydride (4.25 g, 1.5 eq) was added to the reaction solution and was allowed to stir for an additional 24 hours under a blanket of nitrogen. The methanol was removed. The residue was washed with mixture of acetone/hexanes (2:8/v/v, 3×100 ml) and dried in vacuum oven at 50° C. The yield was 9.8 g (60%) of N-acetyl-N-dodecyl D-maltosylamine.

EXAMPLE 2

Preparation of N-Acetyl-N-Tetradecyl D-Maltosylamine in the Absence of a Drying Agent Maltose (10 g), tetradecylamine (5.91 g, 1 eq) were added to methanol (100 ml) at 40°–50° C. for 16 hours. Acetic anhydride (4.25 g, 1.5 eq) was added to the reaction solution and allowed to stir for additional 24 hours under a blanket of nitrogen. The methanol was removed. The residue was washed with a mixture of acetone/hexanes (2:8/v/v, 3×100 ml) and dried in vacuum oven at 50° C. The yield was 9.9 g (58%) of N-acetyl-N-tetradecyl D-maltosylamine.

EXAMPLE 3

Preparation of N-Acetyl-N-Coco D-Maltosylamine in the Absence of a Drying Agent

Maltose (10 g), cocoamine (Adogen$^{(R)}$ 5.58 g, 1 eq) were added to methanol (100 ml) at 40°–50° C. for 16 hours. Acetic anhydride (4.25 g, 1.5 eq) was added to the reaction solution and allowed to stir for an additional 24 hours under a blanket of nitrogen. The methanol was removed. The residue was washed with mixture of acetone/hexanes (2:8/v/v, 3×100 ml) and dried in vacuum oven at 50° C. The yield was 9.1 g (55%) of N-acetyl-N-coco D-maltosylamine.

EXAMPLE 4
Preparation of N-Acetyl-N-Oleyl D-Maltosylamine in the Absence of a Drying Agent Maltose (10 g), oleylamine (7.36 g 1 eq) were added to methanol (100 ml) at 40°–50° C. for 16 hours. Acetic anhydride (4.25 g, 1.5 eq) was added to the reaction solution and allowed to stir for an additional 24 hours under a blanket of nitrogen. The methanol was removed. The residue was washed with a mixture of acetone/hexanes (2:8/v/v, 3×100 ml) and dried in vacuum oven at 50° C. The yield was 10.4 g (60%) of N-acetyl-N-oleyl D-maltosylamine.

EXAMPLE 5
Preparation of N-Acetyl-N-Dodecyl-D-Maltosylamine in the Presence of $Na_2SO_4$ Maltose (10 g), dodecylamine (5.2 g, 1 eq), anhydrous $Na_2SO_4$ (25 g) were added to methanol (100 ml) at 40°–50° C. for 16 hours. Acetic anhydride (4.25 g, 1.5 eq) was added to the reaction solution and allowed to stir for an additional 24 hours under a blanket of nitrogen. The solution was filtered. The methanol was removed. The residue was washed with mixture of acetone/hexanes (2:8/v/v, 3×100 ml) and dried in vacuum oven at 50° C. The yield was 12.6 g (77%) of N-acetyl-N-dodecyl D-maltosylamine.

EXAMPLE 6
Preparation of N-Acetyl-N-Coco D-Maltosylamine in the Presence of $Na_2SO_4$ Maltose (10 g), cocoamine (Adogen[(R)] 5.58 g, 1 eq), anhydrous $Na_2SO_4$ (25 g) were added to methanol (100 ml) at 40°–50° C. for 16 hours. Acetic anhydride (4.25 g, 1.5 eq) was added to the reaction solution and allowed to stir for an additional 24 hours under a blanket of nitrogen. The solution was filtered. The methanol was removed. The residue was washed with mixture of acetone/hexanes (2:8/v/v, 3×100 ml) and dried in vacuum oven at 50° C. The yield was 11.7 g (75%) of N-acetyl-N-coco D-maltosylamine.

EXAMPLE 7
Preparation of N-Acetyl-N-Dodecyl D-Maltosylamine in the Presence of $CaH_2$ Maltose (10 g), dodecylamine (5.2 g, 1 eq), $CaH_2$ (2.3 g, 2 eq) were added to methanol (100 ml) under nitrogen at 40°–50° C. for 16 hours. Acetic anhydride (4.25 g, 1.5 eq) was added to the reaction solution and allowed to stir for additional 24 hours under a blanket of nitrogen. The solution was filtered with filter aid. The methanol was removed. The residue was washed with mixture of acetone/hexanes (2:8/v/v, 3×100 ml) and dried in vacuum oven at 50° C. The yield was 13.1 g (80%) of N-acetyl-N-dodecyl D-maltosylamine.

EXAMPLE 8
Preparation of N-Acetyl-N-Dodecyl D-Glucosylamine in the Presence of $Na_2SO_4$ Glucose (5 g), dodecylamine (5.2 g, 1 eq), anhydrous $Na_2SO_4$ (25 g) were added to methanol (75 ml) at 40°–50° C. for 16 hours. Acetic anhydride (4.25 g, 1.5 eq) was added to the reaction solution and allowed to stir for additional 24 hours under a blanket of nitrogen. The solution was filtered. The methanol was removed. The residue was washed with mixture of acetone/hexanes (2:8/v/v, 3×100 ml) and dried in vacuum oven at 50° C. The yield was 7.97 g (70%) of N-acetyl-N-docecyl D-glucosylamine.

EXAMPLE 9
Preparation of N-Dodecyl-N-Methyl D-Maltosylamide in the Presence of $Na_2S_4$ Maltose monohydrate (40.0 g, 0.111 moles) was reacted with methylamine in methanol (62 ml of a 2.0M solution) and allowed to stir overnight at room temperature. The reaction was allowed to react for 12 hours. Additional methanol 100–125 ml was added to the reaction. After stirring for another hour the solution was clear. Sodium sulfate (30 g) was added to the reaction, stirred for 4–5 hours, filtered and lauric anhydride (45 g, 0.117 moles) was added to the maltosylamine.

The material crude (80 g) was washed with hexanes 2×(500 ml) and washed with 500 ml of acetone to obtain 40 g of a white solid material.

NMR Analysis: $C^{13}$ NMR (DMSO-db)

13.820, 21.99, 22.07, 24.32.57, 39.36, 60. 28.70, 28.77, 28.89, 29.00, 31.27, 32.57, 39.36, 60.76, 68.95, 69.55, 69.78, 72.40, 73.40, 76.80, 77.02, 77.30, 79.48, 85.66, 100.82, 173.20, 173.266.

IR: Nujol mull: OH (3200 $cm^{-1}$), $CH_2$-stretch (2800 $cm^{-1}$), amide I (1640 $cm^{-1}$

Discussion of Example 1–9

From Examples 5–9, it can be seen that the addition of a drying agent such as sodium sulfate ($Na_2SO_4$) or calcium hydride ($CaH_2$) to the reaction mixture, results in improved yields of glycosylamide (70–80%). Reaction mixtures that lack a drying agent (Examples 1–4) do not exhibit high yields of glycosylamide (50–60%).

EXAMPLE 10
Establishment of Efficiency of Drying Agents

|  | Molecular Seive | Na2SO4 | CaH2 |
| --- | --- | --- | --- |
| N-Acetyl-N-$C_{12}$-β-Maltosylamide | 52.7% | 58.6% | 74.2% |
| N-Acetyl-N-$C_{12}$-α-Maltosylamide | 17.0% | 18.9% | 8.4% |
| Maltose | 17.8% | 10.9% | 9.2% |
| $C_{12}$ Amine | 1% | 2.8% | 1.8% |
| N-Acetyl $C_{12}$ Amine | 11.5% | 7.2% | 6.1% |

From the above table it can be seen that acylation of dodecyl maltosylamine with and 2 eq of acetic anhydride in the presence of calcium hydride gave better yields of acetyl $C_{12}$ maltosylamide than those reactions with molecular seive on sodium sulfate ($Na_2SO_4$).

EXAMPLE 11
Establishment of Temperature Criteria

|  | 25° C. | 50° C. | 65° C. |
| --- | --- | --- | --- |
| N-Acetyl-N-$C_{12}$-β-Maltosylamide | 54.5% | 58.6% | 44.3% |
| N-Acetyl-N-$C_{12}$-α-Maltosylamide | 11.0% | 18.9% | 21.7% |
| Maltose | 17.7% | 10.9% | 18% |
| $C_{12}$ Amine | 5.0% | 2.8% | 3.5% |
| N-Acetyl $C_{12}$ Amine | 11.8% | 7.2% | 12% |

From the above table it can be seen that acylation of dodecyl D-maltosylamine with 1.5 eq. of acetic acid at 50° C. gave better yield of N-acetyl-N-dodecyl maltosylamide than those reactions at 25° C. or 50° C. (in the presence of sodium sulfate). All percentages were determined by HPLC.

EXAMPLE 12
Establishment of Order of Addition of Reactants (25°)

|  | AN to MA | MA to AN |
|---|---|---|
| N-Acetyl-N-$C_{12}$-β-Maltosylamide | 58.6% | 45% |
| N-Acetyl-N-$C_{12}$-α-Maltosylamide | 18.9% | 3% |
| Maltose | 10.9% | 15.2% |
| $C_{12}$ Amine | 2.8% | 8.4% |
| N-Acetyl $C_{12}$ Amine | 7.2%  | 10.1% |
| $C_{12}$ Maltosylamine | 0% | 16.6% |

AN = Acetic anhydride
MA = Maltosylamine

From the above table it can be seen that acylation of maltosylamine by adding acetic anhydride to maltosylamine (AN to MA) gave higher yields of N-acetyl-N-dodecyl maltosylamide than adding maltosylamine to acetic anhydride (MA to AN). All percentages were determined by HPLC.

EXAMPLE 13
Preparation of N-Dodecyl-N-Methyl D-Maltosylamide (Scale-Up)

In a 2 L 2-neck round bottom flask equipped with overhead stirrer was added maltose monohydrate (200 g, .584 moles) and 308 ml of 2.0M methylamine in methanol (.614 moles). An additional 700 ml of anhydrous methanol was added to this mixture and was allowed to stir overnight. The non-homogeneous solution turned very thick and pasty compared to what was observed when materials were first added.

Analysis: (Gas Chromatography and C13 NMR) An aliquot of the reaction was taken out of the reaction pot and solvent was removed under reduced pressure to obtain a white powder. This powder was dissolved in DMSO-D6 and C13 spectra as taken and compared to starting maltose. As seen below, the powder was identified as methyl -D-maltosylamine.

N-methyl maltosylamine (C-13NMR, dmso-d6/tms): 31.794, 60.698, 69.749, 72.344, 72.714, 73.197, 73.286, 75.823, 77.059, 80.095, 91.658, 100.774.
I.R.

Nujol mull: OH (3,200 $cm^{-1}$), —$CH_2$— stretch (2800 $cm^{-1}$), amide I (1640 $cm^{-1}$) Lauric anhydride was then added to the reaction pot. Lauric anhydride (TCI) 233 g (.609 moles) was added to the reaction in 25 g parts over a time frame of 30–45 minutes. It was observed when adding the anhydride, that the mixture became less viscous and more free flowing. After reacting over 2 days the reaction became clear. The reaction was then stripped of it's solvent under reduced pressure to yield a crude white solid. This material was then added to 1000 ml. of dry acetone and heated to 50°–55° C. overnight. The solid pot was then filtered and then added to another 1000 ml of acetone and stirred overnight at room temperature. The solids were filtered again and washed with 300 ml of warm acetone and 300 ml of acetone (ambient temperature). The solids were collected and dried overnight to obtain 220 g of off-white solids. Theoretical yield=287 g (77%).

It was found that hexanes wash at room temperature removed most of the fatty acid but left a significant amount of $C_{12}$ amide of methylamine.

EXAMPLE 14
Preparation of N-Dodecyl N-Methyl D-Maltosylamide in the Presence of $Na_2SO_4$ C12-N-Methyl maltosylamide was synthesized by reacting maltose (2.5 g, .007 moles) with 3.5 ml of methylamine (2.0M solution in methanol) at room temperature. This reaction was done at room temperature and began as a non-homogeneous solution. After 12 hours of reaction, the solution was water clear. Sodium sulfate (3 g) was added to the reaction and stirred for 5 hours before 2.68 g (.007 moles) of lauric anhydride was added to the solution at room temperature. The reaction was allowed to go overnight (12 hours) at room temperature. The reaction was followed by I.R. and it indicated formation of glycosylamide and disappearance of the anhydride peak at 1800 $cm^{-1}$.

Workup of the reaction involved removal of the methanol solvent and washing with ethyl acetate (100 ml). After washing, 3.2 g of a white solid material was obtained. Expected theoretical yield=3.75 g. I.R., C13, and 1-H N.M.R. indicated that the product had some minor impurities such as fatty acid and $C_{12}$-amide of methylamine. L.C. analysis indicated 92.50% product, 5.6% fatty acid, 0.5% $C_{12}$-amide of methylamine, and 1.4% unknown.

EXAMPLE 15
Preparation of N-Methyl β-D-Glucosylamine

A one necked round bottom flask equipped with a stir bar was charged with glucose (40.0 g, 0.22 mole) and 2.0M methylamine (116.5 ml, 0.23 mole). The mixture was stirred overnight at room temperature (20°–21° C.). A sample was taken and analyzed by gas chromatography after acetylation.

| Example | Compound | Molar Ratio Glucose:Methylamine | % Purity |
|---|---|---|---|
| 15a | Methyl β-D-Glucosylamine | 1:1 | 88.3 |
| 15b | Methyl β-D-Glucosylamine | 1:1 | 93.3 |
| 15c | Methyl β-D-Glucosylamine | 1:1.05 | 97.6 |
| 15d | Methyl β-D-Glucosylamine | 1:1.05 | 97.6 |

From the above table it can be seen that a slight molar excess of 5% methylamine produces higher yields of N-methyl-β-D-glycosylamine.

EXAMPLE 16
Preparation of N-Dodecyl-N-Methyl D-Glucosylamide 2.5 g of glucose was reacted with 1.05 equivalents of methylamine in methanol to generate the N-methyl glucosylamine. Lauric anhydride (5.28 g, .0138 moles) was added at room temperature to this reaction without drying with sodium sulfate. It was observed that the reaction which was non-homogeneous at first but became clear after 15–20 minutes of reaction time. After 30 minutes, the I.R. of the reaction was taken (neat) and it indicated no carbonyl stretch (1810 $cm^{-1}$) for the anhydride. Gas chromatography analysis (sil-prep derived) showed the following results.

| C12 Fatty Acid | 41.0% |
|---|---|
| C-12 Amide of Methylamine | 1.8% |
| Glucose | 11.0% |
| C12-N-Methyl Glucosylamide | 44.0% |
| Unknown + Others | 1.9% |

EXAMPLE 17
Preparation of N-Dodecyl-N-Methyl D-Glucosylamide and Lauric Acid Mixture D-Glucose (12.67 g, .0703 moles) was reacted with methylamine in methyl alcohol (37–38 ml of a 2.0M solution) at room temperature. This was approximately a 0.05 to 0.06 equivalent excess. The reaction was non-homogeneous and was allowed to run overnight (12 hours), at which it became a clear solution. The reaction was monitored by G.C. by taking 5–6 mg. of the syrupy material and derivitization to its acetate (pyridine/acetic anhydride). The G.C. indicated 99% conversion to the desired glucosylamine product (see gas chromatography). The theoretical amount of water produced in this reaction would be 1.27 g. Sodium sulfate (3 g) was added to the solution before the amidation reaction.

Half of the above solution was taken out and placed in a 100 ml round bottom flask (calculated to contain 6.75 g, 0.0352 moles of N-methyl glucosylamine). It was diluted with another 20–25 ml of anhydrous methanol, and lauric anhydride (13.47 g, 0.0352 moles) was added to the reaction vessel in one shot. The reaction was non-homogeneous when added and the temperature of oil bath was raised to 40° C. The reaction went into solution and was allowed to run overnight.

Analysis by IR suggests reaction was complete. Further analysis by gas chromatography (silated) of this crude reaction mixture showed it contained the following.

| Lauric Acid | 43% |
| C-12 Amide of Methylamine | 5.4% |
| Glucose | 5.0% |
| C12-N-Methyl Glucosylamide | 47% |

The above mixture, which contains mainly lauric acid and C-12-N-methyl glucosylamide, was not purified further and can be used as a mixture in personal product and detergent applications.

EXAMPLE 18

Preparation of N-Dodecyl-N-Methyl D-Glucosylamide (Purification)

Basic resin (Dowex 1×2–100 Resin; (Dowex-1-chloride, anionic 2% cross linking) was used to obtain 1.9 g of crude material which was dissolved in 50 ml of methyl alcohol and a total of 5 g of dry resin was used to remove the acid. The reaction was monitored by I.R. Removal of the methanol gave 1.4 g of a light tan solid. Analysis by gas chromatography showed the following:

| Lauric Acid | 4.9% |
| C-12 Amide of Methylamine | 8.8% |
| Glucose | 4.8% |
| C12-N-methyl Glucosylamide | 82% |

From the above table, it can be seen that the addition of resin can remove most of lauric acid and improve the purity of $C_{12}$-N-methyl D-glucosylamide.

EXAMPLE 19

Preparation of N-Dodecyl-N-Methyl D-Glucosylamide 30 g (.166 mol, 1 eq.) of D-Glucose was mixed with 87.5 ml (2M, 0.175 mol, 1.05 eq.) methylamine (in methanol) and stirred at room temperature overnight. GC showed N-methyl D-glucosylamine and unreacted D-glucose. 9 g of sodium sulfate was added to reaction mixture and stirred for approximately 3 hours to remove any water formed during the reaction. The sodium sulfate was removed by filtration.

63.6 g (.166 mole, 1 eq.) of dodecyl anhydride was added to N-methyl D-glucosylamine, heated to 38° C., allowed to cool to room temperature and stirred overnight to give dodecyl N-methyl D-glucosylamide and lauric acid (verified by GC). The methanol was removed from the pot by rotovap distillation. The N-dodecyl-N-methyl D-glucosylamide was purified by recrystallization of the unreacted lauric anhydride and lauric acid in ethyl acetate. The unreacted D-glucose was removed by recrystallization in water (50% solids).

EXAMPLE 20

Preparation of Dodecyl Methyl D-Glucosylamide (Purification)

In a 100 ml Erlenmeyer was added approximately 5.0 to 5.3 g of crude reaction material. 50 ml of ethyl acetate was added to the flask and heated gently with a heat gun. It was noticed that some of the material went into solution while some did not. The mixture was allowed to sit overnight at room temperature. The solids were filtered off and analyzed after drying giving 2.6 g of slightly tan solid material. Analysis by gas chromatography.

| Lauric acid | 7.2% |
| C12 Amide of Methylamine | 5.0% |
| Glucose | 4.7% |
| C12-N-Methyl Glucosylamide | 83.1% |

From the above table it can be seen that use of ethyl acetate solvent can remove most of the lauric acid and improve the purity of C12-N-methyl D-glucosylamide.

The ethyl acetate layer was analyzed after removal of solvent under reduced pressure to give 2.52 g of a brown solid. Analysis by gas chromatography is shown below:

| Lauric Acid | 75.8% |
| C12 Amide of Methylamine | 15.0% |
| Glucose | negligible |
| Unknown | 1.2% |
| C12-N-Methyl Glucosylamide | 8.0% |

From the above table, it can be seen that the ethyl acetate solvent contains most of the lauric acid.

EXAMPLE 21

Establishment of the Order of Addition

C12-N-Methyl Glucosylamide Synthesis:

A study on the order of addition of N-methyl glucosylamine to C12 anhydride and C12 anhydride to N-methyl glucosylamine was conducted. Four reactions were run in which we studied the effect of addition on the conversion of N-methylglucosylamine to the amide. One set of experiments was done with the drying of the glucosylamine with sodium sulfate while the other set looked at effects without drying.

Study #1 (Addition of reagents without sodium sulfate drying)

Two reactions were run simultaneously where D-glucose (2.5 g, .0139 moles) was reacted with 7.3 ml of a 2.0M solution of methylamine. The reaction went to completion and was used for the amidation step to follow.

Amine Added to Anhydride:

In a dry 14/20 two-neck 50 ml round bottom flask was added lauric anhydride (5.32 g, .0139 moles) and 20 ml of anhydrous methanol. This mixture was heated to 40° C. (bath temperature) when it became more homogeneous. The N-methyl glucosylamine solution was added at a rate of 1 drop/40 seconds for 1 hour then 1 drop/5 seconds for 1 hour. The total addition time was 2 hours at 40° C. After these 2 hours, the oil bath was removed and reaction allowed to run at room temperature overnight.

Analysis by Gas Chromatography:

| Compound | Relative amounts |
| --- | --- |
| C12 Methyl Ester | 9.30% |
| Fatty Acid | 41.05% |
| C12 Amide of Methylamine | 5.70% |

-continued

| Compound | Relative amounts |
|---|---|
| D-Glucose | 8.27% |
| C12-N-Methyl Glucosylamide | 35.67% |

Anhydride Added to Amine:

In this reaction the parameters are the same as the reaction above but the order of addition is reversed. The anhydride in methanol (heated by heat gun) was added to the N-methyl glucosylamine at 40° C.

Analysis by Gas Chromatography:

| Compound | Relative amounts |
|---|---|
| C12 Methyl Ester | 3.0% |
| C12 Fatty Acid | 49.0% |
| C12 Amide of Methylamine | 9.7% |
| D-Glucose | 21.0% |
| C12-N-Methyl Glucosylamide | 15.5% |

This shows amine to anhydride gives more product and less by-product(s), i.e., amide of methylamine.

EXAMPLE 22

Establishment of the Order of Addition

Study #2 (Addition of sodium sulfate)

Amine to Anhydride

The same moles of reagents were used as in the above experiments except the variable that was changed here was addition of sodium sulfate (3 g) to the reactions and stirring them overnight (12 hrs.), filtering the salt before using them for the next step. The addition ratio was faster (1 drop/10 seconds): Total time=1 hr: Temp.=40° C.

Gas Chromatograph Analysis:

| Compound | Relative amounts |
|---|---|
| C12 Methyl Ester | 7.0% |
| C12 Fatty Acid | 40.0% |
| C12 Amide of Methylamine | 6.45% |
| D-Glucose | 5.90% |
| C12-N-Methyl glucosylamide | 38.50% |

Anhydride to Amine:

The lauric anhydride was dissolved in methanol (kept in solution by heating with a heat gun) and added to a solution of N-methyl glucosylamine. The reagent amounts were the same as in study #1. (Example 21)

Gas Chromatography Analysis:

| Compound | Relative amounts |
|---|---|
| C12 Methyl Ester | 3.6% |
| C12 Fatty Acid | 45.6% |
| C12 Amide of Methylamine | 2.0% |
| D-Glucose | 15.2% |
| C12-N-Methyl Glucosylamide | 34.0% |

Based on these observations (Example 21 and 22), the critical parameters in the conversion of N-methyl glucosylamine to the amide depends on the removal of water formed in the amine formation. The conversion of the amine to amide in Study #2 was improved at 40° C. when the amine was added to the anhydride, instead of anhydride added to the amine.

EXAMPLE 23

Synthesis of N-Hexadecyl-D-Glucosylamine

A 2 L two neck round bottom flask equipped with condenser was charged with D(+) glucose (60 g, 0.333 moles), 2-propanol (900 mL), hexadecylamine (81 g, 0.334 moles) and deionized water (300 mL). The reaction was stirred and heated to 50°–55° celsius for 1 hour to obtain a homogeneous solution. The reaction was then allowed to run overnight at room temperature. The reaction precipitated out after 2–3 hours.

Reaction Workup

The reaction mixture above was filtered through a large Buchner funnel using Whatman (40) filter paper and placed in a vacuum oven overnight.

Purification of N-Hexadecyl-D-Glucosylamine

In 800 mL of absolute ethanol (200 proof) was added 60 g of the crude N-hexacecyl-D-glucosylamine. The mixture was refluxed until material was soluble and then cooled to room temperature. Crystalline material formed after 3 hours and was filtered.

Proton NMR (DMSO-d6): 0.821 (triplet, CH3), 1.24 (broad singlet, —CH2—), 2.14 (singlet, NH), 2.7–3.6 (multiplet, CH-OH) 4.3–4.4 (doublet).

Melting point: 100°–110° C. (with decomposition at ~110° C.).

EXAMPLE 24

Synthesis of N-Hexadecanamide, -N-Headecyl D-Glucopyranosyl Amide

A two neck 250 mL round bottom flask equipped with nitrogen inlet and condensor was charged with N-hexadecyl-D-glucosylamine (4 g, 0.010 moles), anhydrous tetrahydrofluran (150 mL) and 2 mL of triethylamine. The reaction was stirred and chilled with ice bath. Pamitoyl chloride (2.75 g, 0.010 moles) was added to 25 mL of dry THF in an addition funnel and added dropwise. The reaction was allowed to go overnight at room temperature.

The reaction was monitored by thin layer chromatography (20:1 methylene chloride/methanol v/v). The reaction showed 3 major components with Rf values of 0.63 (palmitic acid), 0.44 (amide ester?), 0.22, respectively. The reaction was worked up by removing the solvent under reduced pressure and column chromatography with the solvent system above. The purest fractions were collected and using IR, NMR, C13 and 1H NMR analysis, the fraction with Rf value of 0.22 was the compound of interest (yield 1.5 g), 25%.

This compound is useful as a fabric softener for fabric softening compositions.

EXAMPLE 25

Foam Height and Krafft Temperature

Krafft temperatures for N-acetyl $C_{12}$, $C_{14}$ and cocomaltosylamides were measured and compared with C12 methyl D-glucamide (a non-cyclic sugar surfactant). The results are set forth below.

| | T (Krafft) | Foam Height in Millimeters (Initial) | Foam Height in Millimeters (Final) |
|---|---|---|---|
| N-Acetyl C12 Maltosylamide | <5° C. | 150 | 145 |
| N-Acetyl C14 Maltosylamide | <5° C. | 110 | 105 |
| N-Acetyl Coco Maltosylamide | <5° C. | 155 | 150 |
| C12 Methyl D-Glucamide (Comparative) | 45.3° C. | 173 | 158 |

The results showed that certain maltosylamides have lower Krafft points than $C_{12}$ methyl D-glucamide a comparative sugar surfactant.

It should be noted that the Krafft point of a surfactant is the temperature at which a surfactant will form micelles and provide good foaming and/or detergency. Compounds that do not have favorable Krafft points (compounds which have high Krafft points) are less soluble in water and will not form micelles necessary for good foaming and/or detergency.

EXAMPLE 26—Detergency

The detergency for N-acetyl coco maltosylamide and N-acetyl $C_{14}$ maltosylamide were compared to that of Neodol 25-7 (typical nonionic surfactant used in detergents). The improvement in detergency was determined on a reflectometer and was measured as $\Delta R$. This is defined as the change in reflectance of swatches before and after washing ($\Delta R = R_{bW} - R_{aw}$ wherein $R_{bW}$ is the reflectance before washing and $R_{aw}$ is the reflectance after washing). In general higher $\Delta R$ values suggest better cleaning or improved detergency.

| Surfactant | $\Delta R$ |
| --- | --- |
| Neodol 25-7 (Comparative) | 16.3 |
| N-Acetyl Coco MTA | 16.2 |
| N-Acetyl $C_{14}$ MTA | 15.9 |

As can be seen from the above, the results show that N-acetyl coco and N-acetyl $C_{14}$ maltosylamide (MTA) are comparable to Neodol 25-7 in terms of detergency.

The wash conditions used were as follows.

| | |
| --- | --- |
| Surfactant (Neodol 25-7, Acetyl Coco MTA or Acetyl $C_{14}$ MTA) | 0.22 g/l |
| Zeolite | 0.45 g/l |
| Sodium Carbonate | 0.30 g/l |
| pH | 10 |
| Hardness | 120 ppm (2:1 Ca:Mg) |
| Wash Time | 15 minutes |

EXAMPLE 27—Detergency

As shown in FIG. 1, a ternary surfactant system of 1–80% LAS (linear benzene sulfonate) and 20–99% of mixture of 75% Neodol 25-7 ($C_{12}$–$C_{15}$ alcohol ethoxylate +7 moles of ethylene oxide) and 25% acetyl $C_{14}$ MTA provides better detergency than a binary surfactant system of 1–80% LAS and 20–99% Neodol 25-7 alone.

The wash conditions used were as follows:

| | |
| --- | --- |
| Surfactant (Neodol 25-7 or Acetyl $C_{14}$ MTA) | 0.22 g/l |
| Zeolite | 0.45 g/l |
| Sodium Carbonate | 0.30 g/l |
| pH | 10 |
| Hardness | 120 ppm (2:1 Ca:Mg) |
| Wash Time | 15 minutes |

EXAMPLE 28—Detergency

Figure 2:
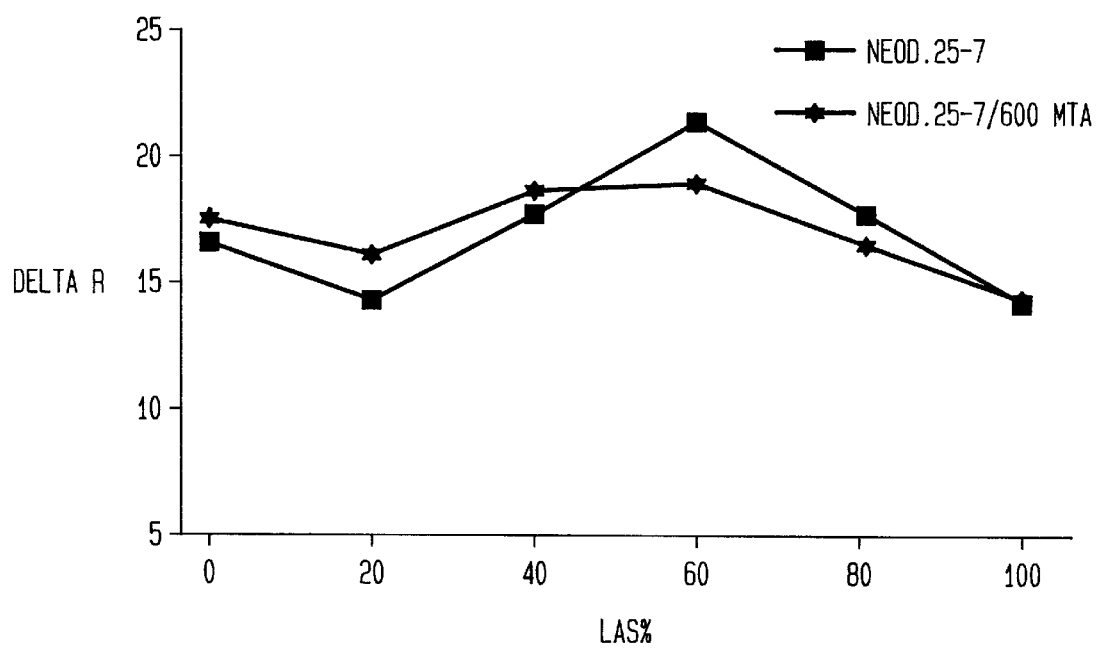
FIG. 2 shows detergency results in a ternary system comprising LAS (linear alkylbenzenesulfonate) and a mixture of 75% Neodol 25–7 ($C_{12}$–$C_{15}$ alkyl alcohol with 7 moles of ethylene oxide) and 25% COCO MTA (N-acetyl coconut maltosylamide). From FIG. 2 it can be seen that the tertiary maltosylamide system is slightly better or about the same as a binary system without maltosylamide.

As shown in FIG. 2, a ternary surfactant system of 1–47% LAS (linear benzene sulfonate) and 53–94% of mixture of 75% Neodol 25-7 ($C_{12}$–$C_{15}$ alcohol ethoxylate +7 moles of ethylene oxide) and 25% of acetyl Coco MTA provides better detergency than a binary surfactant system of 1–47% LAS and 53–99% Neodol 25-7 alone.

The wash conditions used were as follows:

| | |
| --- | --- |
| Surfactant (Neodol 25-7 or Acetyl Coco MTA) | 0.22 g/l |
| Zeolite | 0.45 g/l |
| Sodium Carbonate | 0.30 g/l |
| pH | 10 |
| Hardness | 120 ppm (2:1 Ca:Mg) |
| Wash Time | 15 minutes |

EXAMPLE 29

SURFACTANCY

In order to determine the effectiveness of these compounds as a surfactant, various physical properties (i.e., CMC Krafft point, CMC and area per molecule of the surfactant (which are associated with how "good" a surfactant is) were measured. These are set forth below in the table comparing $C_{12}$ methyl glucosylamide to $C_{12}$ methyl glucamide.

TABLE COMPRISING PHYSICAL PROPERTIES
OF $C_{12}$-METHYL GLUCOSYLAMIDE TO $C_{12}$-METHYL GLUCAMIDE

| | $C_{12}$-METHYL GLUCOSYLAMIDE | $C_{12}$-METHYL GLUCAMIDE (Comparative) |
| --- | --- | --- |
| Krafft Point | 37° C. | 45.3° C. |
| C.M.C. | $4.97 \times 10^{-5}$ M | $4.3 \times 10^{-4}$ M |
| Area/Molecule | 41.1 | 37.3 |
| Structure | (pyranose ring structure with N–C(=O)–$C_{11}H_{23}$ and N–CH$_3$) | (open-chain polyol structure with N–C(=O)–$C_{11}H_{23}$ and N–CH$_3$) |

From the above table it can be seen that the surfactant properties of $C_{12}$ methyl glucosylamide are comparable to that of $C_{12}$ methyl glucamide. Therefore, this finding suggests that $C_{12}$ methyl glucosylamide should behave similarly to that of $C_{12}$ methylglucamide in both detergent and personal product applications. Glycosylamides provide favorable surfactant benefits.

EXAMPLE 30

Deposition of N-Tallow-N-Acetyl-D-Maltosylamide (Fabric Softening Applications)

A deposition study on N-tallow-N-acetyl-D-maltosylamide was done using HPLC. Two independent tests were performed and an average value was calculated to obtain the final results displayed below.

HPLC Condition

Column: Hexyl, 5 micron, 15 cm×4.6 mm temp.=35° C.
Detector: RI, 35° C.
Solvent: Acetonitrile/methanol/water (25/25/50); PH=3.0; 7 g $NaClO_4$/L

| Time (Min) | % Absorbed |
|---|---|
| 0 | 0% |
| 1 | 68.8% |
| 3 | 74.7% |
| 5 | 74.7% |

This example shows that tallow acetyl D-maltosylamide deposits on to terry cloths amides are useful as fabric softeners in fabric softening compositions.

EXAMPLE 31

A detergent composition can be made using mixture of reaction products from Example 17 which is a powdered composition as follows:

(1) 1–50% detergent active of the following mixture. 47% C12-N-methyl glycosylamide, 43% lauric acid, 5.4% C12-N-methylamide, 5% glucose;
(2) 0–50% surfactant;
(3) 0–40% builder;
(4) 0–30% buffer salt;
(5) 0–30% sulfate;
(6) 0–20% bleach system;
(7) 0–4% enzyme;
(8) minors plus water to 100%

EXAMPLE 32

A detergent composition can be made using mixture of reaction products from Example 17 which is a liquid composition as follows:

(1) 1–70% detergent active of the following mixture: 47% C12-N-methyl glycosylamide, 43% lauric acid, 5.4% C12-N-methylamide, 5% glucose;
(2) 0–50% surfactant;
(3) 0–50% builder;
(4) 0–40% electrolyte;
(5) 0.01–5% enzyme;
(6) 0.1–15% enzyme stabilizer;
(7) 0–20% phase regulant;
(8) minors plus water to 100%

We claim:

1. A personal product composition comprising a glycosylamide wherein said glycosylamide has the structure:

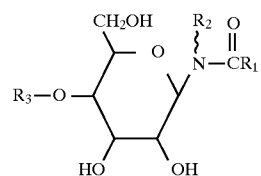

wherein $R_1$ is hydrogen or a substituted or unsubstituted straight chain or branched, saturated or unsaturated alkyl group having 1 to 30 carbons;

$R_2$ is hydrogen or a substituted or unsubstituted straight chain or branched, saturated or unsaturated alkyl, cycloalkyl, alkyl cycloalkyl, or aralkyl having 1 to 30 carbons; and $R_3$ is a glycosyl radical or hydrogen;

wherein, if $R_2$ is hydrogen, $R_1$ must contain an interrupting heteroatom group;

wherein the composition is selected from the group consisting of a toilet bar soap, a facial body cleanser, a shampoo, a conditioner composition, a cosmetic composition, a shaving cream, a shaving lotion, a shower gel, a fabric softening conditioner composition, and an underarm deodorant/antiperspirant composition.

2. A composition according to claim 1, comprising the following:

| Ingredients | % by Weight |
|---|---|
| Fatty Acid | 5–60 |
| Glycosylamide | 0.1–4 |
| Alkyl or Aryl Sulfate or sulfonate | 0–5 |
| Coactive other than Glycosylamide | 0–10 |
| Sorbitol | |
| Cellulose | 0–0.5 |
| Sequestering agent | 0.1–0.5 |
| Water and minors | to Balance |

3. A composition according to claim 1 wherein the composition is a shampoo, comprising

| Ingredients | |
|---|---|
| Glycosylamide | 0.1–35 |
| Anionic coactive | 0–10 |
| Amphoteric coactive | 0–10 |
| Lauramide MEA | 0–5 |
| Thickener | 0–5 |
| Fragrance | 0–2 |
| Preservative | 0–1% |
| Water and minors | to Balance |

* * * * *